United States Patent
Iwasaki et al.

(10) Patent No.: US 11,513,174 B2
(45) Date of Patent: Nov. 29, 2022

(54) MAGNETIC SENSOR AND INSPECTION DEVICE

(71) Applicant: KABUSHIKI KAISHA TOSHIBA, Tokyo (JP)

(72) Inventors: Hitoshi Iwasaki, Nerima Tokyo (JP); Satoshi Shirotori, Yokohama Kanagawa (JP); Akira Kikitsu, Yokohama Kanagawa (JP); Yoshihiro Higashi, Komatsu Ishikawa (JP); Kenichiro Yamada, Minato Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 17/400,860

(22) Filed: Aug. 12, 2021

(65) Prior Publication Data
US 2022/0221535 A1    Jul. 14, 2022

(30) Foreign Application Priority Data
Jan. 13, 2021    (JP) .............................. JP2021-003268

(51) Int. Cl.
*G01R 33/02*    (2006.01)
*G01R 33/09*    (2006.01)
*G01R 31/382*    (2019.01)
*A61B 5/245*    (2021.01)

(52) U.S. Cl.
CPC .......... *G01R 33/093* (2013.01); *G01R 31/382* (2019.01); *A61B 5/245* (2021.01)

(58) Field of Classification Search
CPC .. G01R 31/382; G01R 33/093; G01R 33/091; G01R 33/098
See application file for complete search history.

(56) References Cited

U.S. PATENT DOCUMENTS

2018/0271395 A1    9/2018    Iwasaki et al.

FOREIGN PATENT DOCUMENTS

JP    2018-155719 A    10/2018

*Primary Examiner* — Alesa Allgood
(74) *Attorney, Agent, or Firm* — Finnegan, Henderson, Farabow, Garrett & Dunner, LLP

(57) ABSTRACT

According to one embodiment, a magnetic sensor includes a first magnetic element, a conductive member including a first corresponding portion, an element current circuit configured to supply an element current to the first magnetic element, and a first current circuit configured to supply a first current to the first corresponding portion. The first corresponding portion is along the first magnetic element. The first current includes an alternating current component. The first current includes a first duration of a first current value of a first polarity, a first pulse duration of a first pulse current value of the first polarity, a second duration of a second current value of a second polarity, and a second pulse duration of a second pulse current value of the second polarity. The second polarity is different from the first polarity.

20 Claims, 16 Drawing Sheets

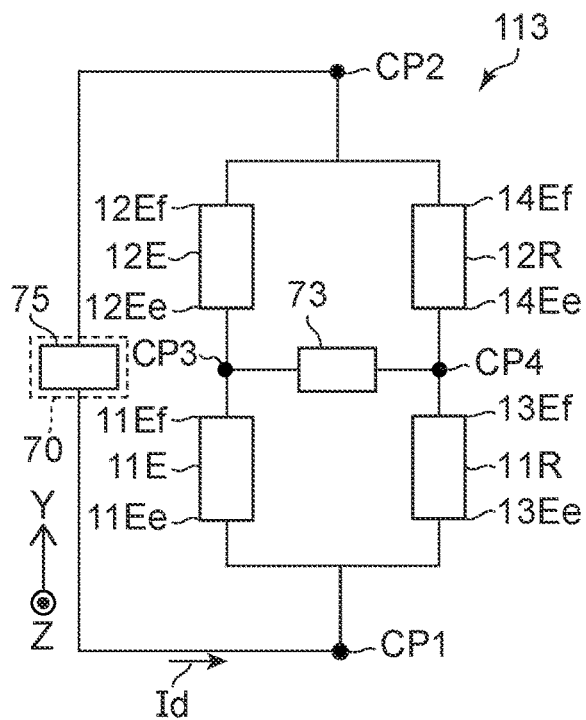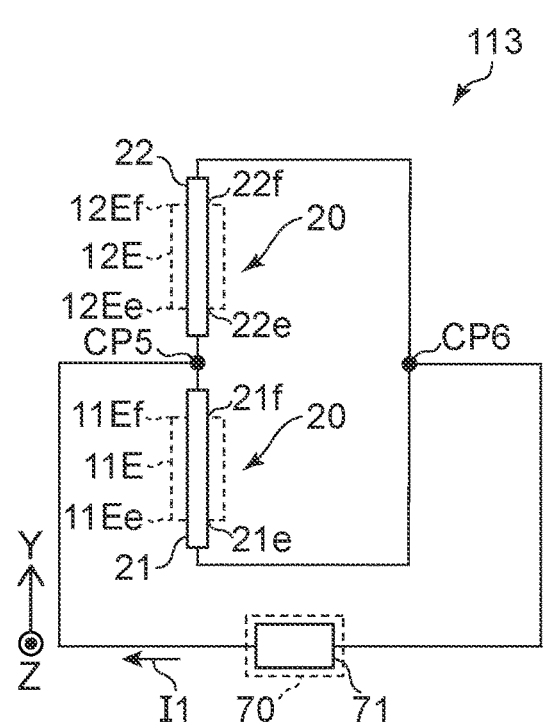
FIG. 13A    FIG. 13B
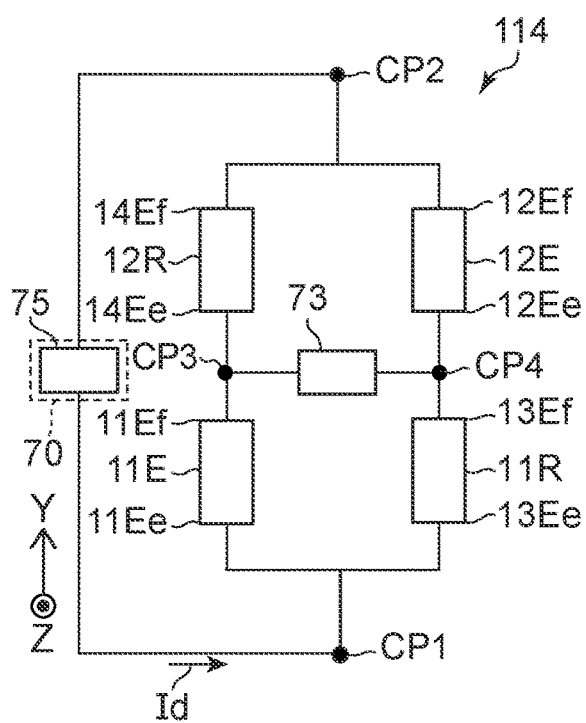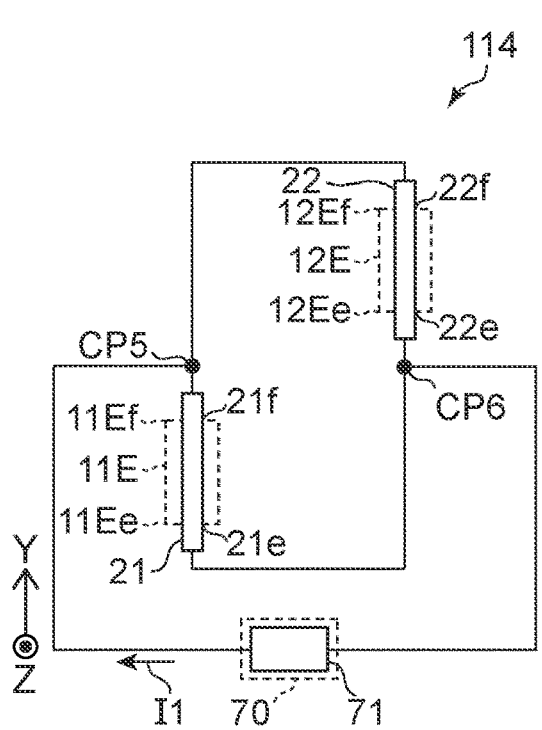
FIG. 14A    FIG. 14B

MAGNETIC SENSOR AND INSPECTION DEVICE

CROSS-REFERENCE TO RELATED APPLICATIONS

This application is based upon and claims the benefit of priority from Japanese Patent Application No. 2021-003268, filed on Jan. 13, 2021; the entire contents of which are incorporated herein by reference.

FIELD

Embodiments described herein relate generally to a magnetic sensor and an inspection device.

BACKGROUND

There is a magnetic sensor that uses a magnetic layer. There is an inspection device that uses the magnetic sensor. It is desirable to increase the sensitivity of the magnetic sensor.

BRIEF DESCRIPTION OF THE DRAWINGS

FIGS. 13A and 13B are schematic plan views illustrating a magnetic sensor according to the second embodiment;

FIGS. 14A and 14B are schematic plan views illustrating a magnetic sensor according to the second embodiment;

DETAILED DESCRIPTION

Figure 1A:
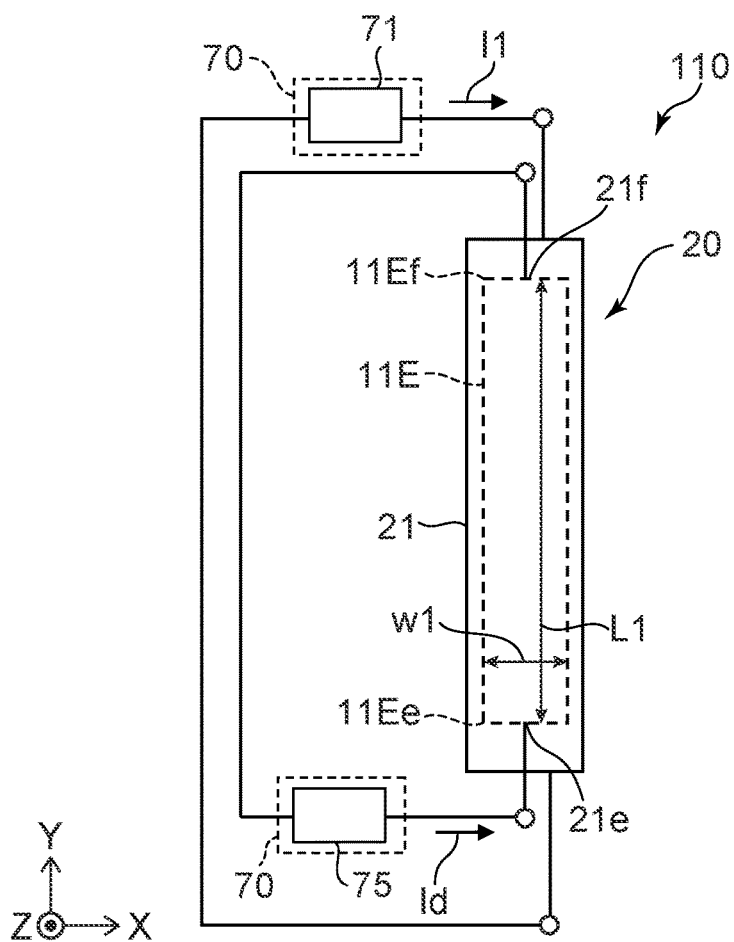
FIGS. 1A to 1C are schematic views illustrating a magnetic sensor according to a first embodiment.

According to one embodiment, a magnetic sensor includes a first magnetic element, a conductive member including a first corresponding portion, an element current circuit configured to supply an element current to the first magnetic element, and a first current circuit configured to supply a first current to the first corresponding portion. The first corresponding portion is along the first magnetic element. The first current includes an alternating current component. The first current includes a first duration of a first current value of a first polarity, a first pulse duration of a first pulse current value of the first polarity, a second duration of a second current value of a second polarity, and a second pulse duration of a second pulse current value of the second polarity. The second polarity is different from the first polarity. An absolute value of the first pulse current value is greater than an absolute value of the first current value and greater than an absolute value of the second current value. An absolute value of the second pulse current value is greater than the absolute value of the first current value and greater than the absolute value of the second current value. The first pulse duration is less than the first duration and less than the second duration. The second pulse duration is less than the first duration and less than the second duration.

According to one embodiment, a magnetic sensor includes a first magnetic element, a conductive member including a first corresponding portion, an element current circuit configured to supply an element current to the first magnetic element, and a first current circuit configured to supply a first current to the first corresponding portion. The first corresponding portion is along the first magnetic element. The first current includes an alternating current component. The first current includes a first duration of a first current value of a first polarity, and a second duration of a second current value of a second polarity. The second polarity is different from the first polarity. The element current includes a first sub-duration of a first element value of the first polarity, a first sub-pulse duration of a first pulse element value of the first polarity, a second sub-duration of a second element value of the second polarity, and a second sub-pulse duration of a second pulse element value of the second polarity. The first sub-duration is a portion of the first duration. The first sub-pulse duration is an other portion of the first duration. The second sub-duration is a portion of the second duration. The second sub-pulse duration is an other portion of the second duration. An absolute value of the first pulse element value is greater than an absolute value of the first element value and greater than an absolute value of the second element value. An absolute value of the second pulse element value is greater than the absolute value of the first element value and greater than the absolute value of the second element value. The first sub-pulse duration is less than the first sub-duration and less than the second sub-duration. The second sub-pulse duration is less than the first sub-duration and less than the second sub-duration.

According to one embodiment, an inspection device includes the magnetic sensor described above, and a processor configured to process a signal output from the magnetic sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
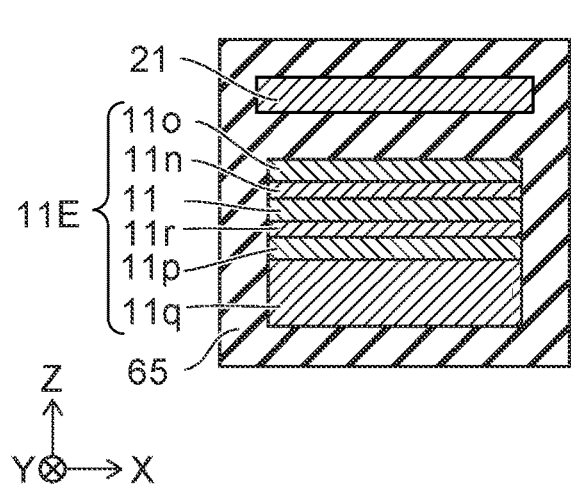
Figure 1C:
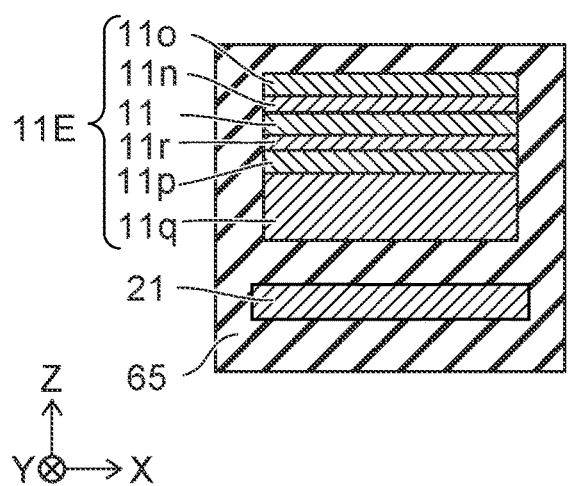

FIGS. 1A to 1C are schematic views illustrating a magnetic sensor according to a first embodiment. FIG. 1A is a plan view. FIG. 1B is one example of a cross-sectional view. FIG. 1C is another example of a cross-sectional view.

As shown in FIG. 1A, the magnetic sensor 110 according to the embodiment includes a first magnetic element 11E, a conductive member 20, an element current circuit 75, and a first current circuit 71.

The conductive member 20 includes a first corresponding portion 21. The first corresponding portion 21 is along the first magnetic element 11E.

The first magnetic element 11E includes a first end portion 11Ee and a first other-end portion 11Ef. The direction from the first end portion 11Ee toward the first other-end portion 11Ef is taken as a first direction. The first direction is taken as a Y-axis direction. A direction perpendicular to the Y-axis direction is taken as an X-axis direction. A direction perpendicular to the Y-axis direction and the X-axis direction is taken as a Z-axis direction.

The length along the first direction (the Y-axis direction) of the first magnetic element 11E is taken as a first length L1. The length along the second direction of the first magnetic element 11E is taken as a first width w1. A second direction crosses the first direction. The second direction is, for example, the X-axis direction. The first length L1 is greater than the first width w1.

As shown in FIGS. 1B and 1C, for example, the direction from the first magnetic element 11E toward the first corresponding portion 21 is along a third direction. The third direction crosses a plane including the first and second directions. The third direction is, for example, the Z-axis direction. In the example, the first corresponding portion 21 overlaps the first magnetic element 11E in the Z-axis direction.

As shown in FIG. 1A, for example, the first corresponding portion 21 includes a first portion 21e and a first other-portion 21f. The first portion 21e corresponds to the first end portion 11Ee. The first other-portion 21f corresponds to the first other-end portion 11Ef. For example, the first portion 21e overlaps the first end portion 11Ee in the Z-axis direction. The first other-portion 21f overlaps the first other-end portion 11Ef in the Z-axis direction.

As shown in FIG. 1A, the element current circuit 75 is configured to supply an element current Id to the first magnetic element 11E. The element current Id flows between the first end portion 11Ee and the first other-end portion 11Ef.

As shown in FIG. 1A, the first current circuit 71 is configured to supply a first current I1 that includes an alternating current component to the first corresponding portion 21. For example, the first current circuit 71 supplies the first current I1 between the first portion 21e and the first other-portion 21f. The element current circuit 75 and the first current circuit 71 may be included in a circuit part 70. The direction in which the first current I1 flows is along the direction (e.g., the Y-axis direction) in which the element current Id flows. For example, the direction of the element current Id and the direction of the first current I1 cross the direction of the magnetic field of the detection object.

A magnetic field of the detection object is applied to the first magnetic element 11E. For example, the magnetic field of the detection object has an X-axis direction component. The electrical resistance of the first magnetic element 11E changes according to the magnetic field of the detection object. For example, the electrical resistance of the first magnetic element 11E corresponds to the electrical resistance between the first end portion 11Ee and the first other-end portion 11Ef.

As shown in FIGS. 1B and 1C, for example, the first magnetic element 11E includes a first magnetic layer 11, a first counter magnetic layer 11o, and a first nonmagnetic layer 11n. The first nonmagnetic layer 11n is located between the first magnetic layer 11 and the first counter magnetic layer 11o.

For example, the angle between the orientation of the magnetization of the first magnetic layer 11 and the orientation of the magnetization of the first counter magnetic layer 11o changes according to the magnetic field applied to the first magnetic element 11E. The electrical resistance of the first magnetic element 11E changes due to the change of the angle.

According to the embodiment, the first magnetic element 11E may include a first layer 11q. The first layer 11q includes, for example, at least one selected from the group consisting of IrMn and PtMn. The first layer 11q is, for example, an antiferromagnetic layer. The first magnetic layer 11 is between the first layer 11q and the first counter magnetic layer 11o.

The first magnetic element 11E further includes, for example, an intermediate magnetic layer 11p and an intermediate nonmagnetic layer 11r. The intermediate magnetic layer 11p is between the first layer 11q and the first magnetic layer 11. The intermediate nonmagnetic layer 11r is between the intermediate magnetic layer 11p and the first magnetic layer 11. In one example, the first nonmagnetic layer 11n includes at least one selected from the group consisting of Cu, Au, and Ag. For example, the first nonmagnetic layer 11n is a Cu layer. The intermediate nonmagnetic layer 11r includes, for example, Ru. The first magnetic element 11E is, for example, a GMR (Giant Magnetic Resistance) element.

At least one of the first magnetic layer 11, the first counter magnetic layer 11o, or the intermediate magnetic layer 11p includes, for example, at least one selected from the group consisting of CoFe, CoFeNi, and NiFe.

According to the embodiment, the first layer 11q, the intermediate magnetic layer 11p, and the intermediate nonmagnetic layer 11r are provided as necessary and may be omitted.

As shown in FIGS. 1B and 1C, the magnetic sensor 110 may include an insulating member 65. At least a portion of the insulating member 65 may be located between the first magnetic element 11E and the first corresponding portion 21. At least a portion of the insulating member 65 may be located around the first magnetic element 11E and the first corresponding portion 21.

As shown in FIG. 1B, the first counter magnetic layer 11o may be located between the first magnetic layer 11 and the first corresponding portion 21. As shown in FIG. 1C, the first magnetic layer 11 may be located between the first corresponding portion 21 and the first counter magnetic layer 11o.

As described above, the first current I1 that includes the alternating current component is supplied to the first corresponding portion 21. A current magnetic field that is based on the first current I1 is applied to the first magnetic element 11E. The electrical resistance of the first magnetic element 11E changes according to the magnetic field of the detection object and the current magnetic field based on the first current I1. For example, the magnetic field of the detection object can be detected with high sensitivity by processing the detected change of the electrical resistance according to the frequency of the alternating current component of the first current I1. An example of the change of the electrical resistance is described below.

An example of the element current Id and the first current I1 will now be described.

Figure 2A:
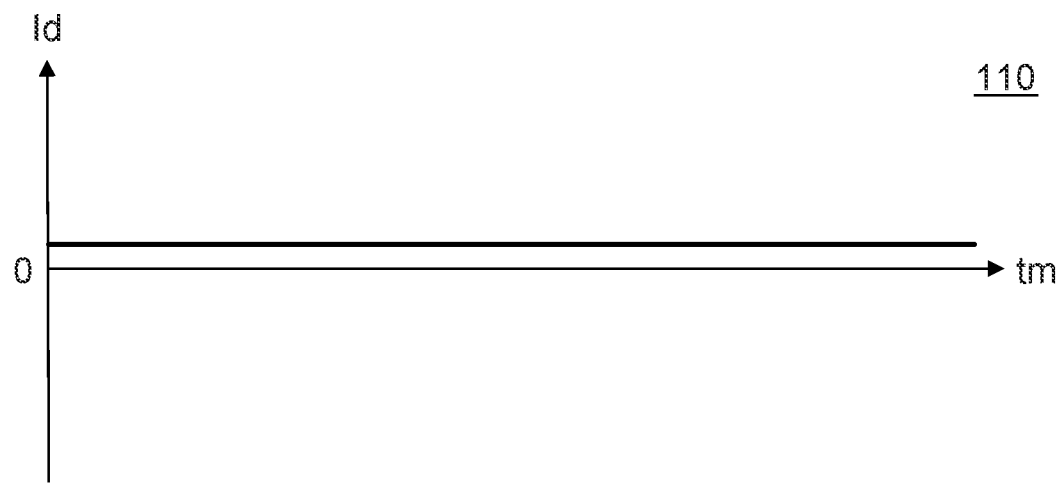
FIGS. 2A and 2B are schematic views illustrating the magnetic sensor according to the first embodiment.
Figure 2B:
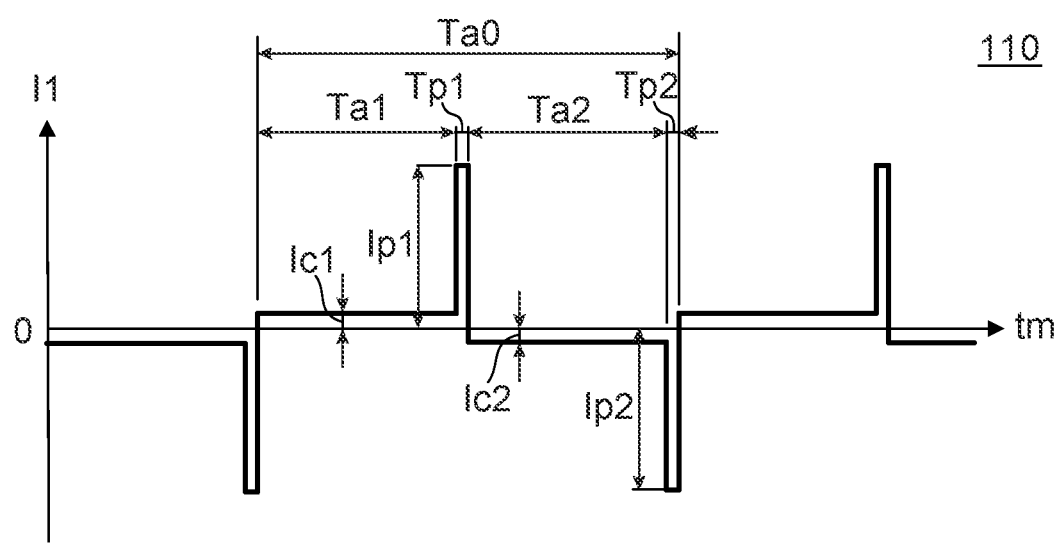

FIGS. 2A and 2B are schematic views illustrating the magnetic sensor according to the first embodiment.

In FIGS. 2A and 2B, the horizontal axis is a time tm. The vertical axis of FIG. 2A is the value of the element current Id. The vertical axis of FIG. 2B is the value of the first current I1.

In the example as shown in FIG. 2A, the element current Id is substantially constant. The element current Id is, for example, a direct current.

In the example as shown in FIG. 2B, the first current I1 includes a first duration Ta1, a first pulse duration Tp1, a second duration Ta2, and a second pulse duration Tp2. The first current I1 has a first current value Ic1 of a first polarity in the first duration Ta1. The first current I1 has a first pulse current value Ip1 of the first polarity in the first pulse duration Tp1. The first current I1 has a second current value Ic2 of a second polarity in the second duration Ta2. The first current I1 has a second pulse current value Ip2 of the second polarity in the second pulse duration Tp2. The second polarity is different from the first polarity. For example, the first polarity is one of positive or negative. The second polarity is the other of positive or negative.

For example, the sum of the first duration Ta1, the first pulse duration Tp1, the second duration Ta2, and the second pulse duration Tp2 corresponds to a period Ta0 of the alternating current component of the first current I1. For example, the first duration Ta1 and the first pulse duration Tp1 are a first polarity duration (e.g., a positive duration). For example, the second duration Ta2 and the second pulse duration Tp2 are a second polarity duration (e.g., a negative duration).

The absolute value of the first pulse current value Ip1 is greater than the absolute value of the first current value Ic1 and greater than the absolute value of the second current value Ic2. The absolute value of the second pulse current value Ip2 is greater than the absolute value of the first current value Ic1 and greater than the absolute value of the second current value Ic2.

The first pulse duration Tp1 is less than the first duration Ta1 and less than the second duration Ta2. The second pulse duration Tp2 is less than the first duration Ta1 and less than the second duration Ta2.

Thus, according to the embodiment, the first current I1 includes the first pulse current value Ip1 and the second pulse current value Ip2 that have pulse forms in addition to the first and second current values Ic1 and Ic2 that are alternating currents. As described below, for example, a substantially even-function change occurs when the electrical resistance of the first magnetic element 11E in the first polarity duration and the electrical resistance of the first magnetic element 11E in the second polarity duration are temporally combined. Thereby, as described below, it is possible to suppress noise and detect the magnetic field of the detection object with high sensitivity.

An example of the electrical resistance of the first magnetic element 11E will now be described.

Figure 3A:
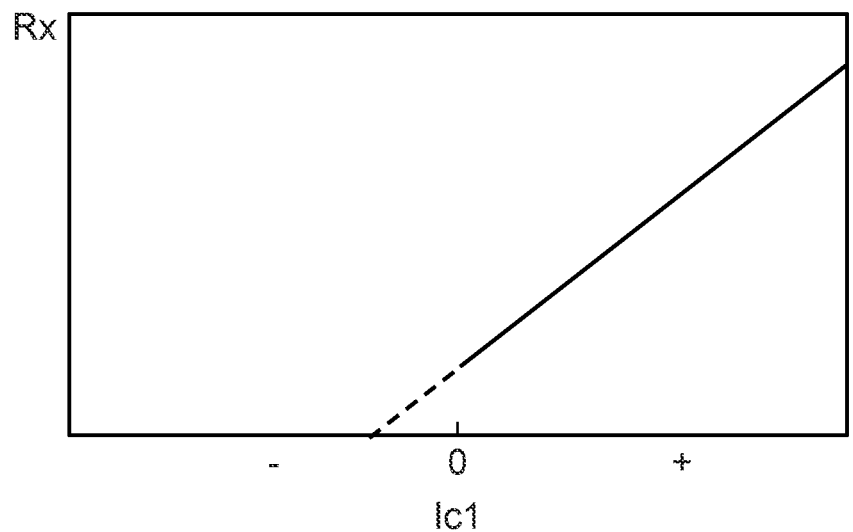
FIGS. 3A and 3B are schematic views illustrating characteristics of the magnetic sensor according to the first embodiment.
Figure 3B:
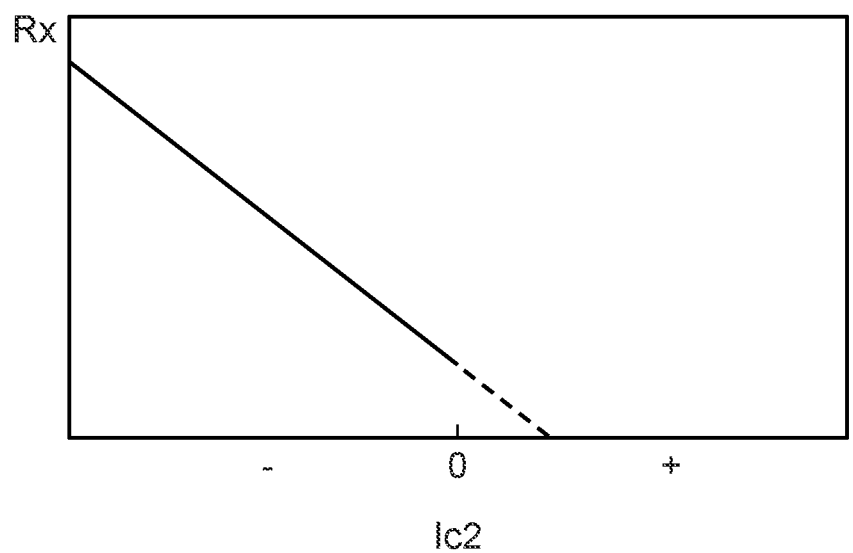

FIGS. 3A and 3B are schematic views illustrating characteristics of the magnetic sensor according to the first embodiment.

The horizontal axis of FIG. 3A is the first current value Ic1. The horizontal axis of FIG. 3B is the second current value Ic2. In FIGS. 3A and 3B, the vertical axis is an electrical resistance Rx of the first magnetic element 11E. FIG. 3A illustrates the change of the electrical resistance Rx when the absolute value of the first current value Ic1 of the first polarity changes in the first polarity duration. FIG. 3B illustrates the change of the electrical resistance Rx when the absolute value of the second current value Ic2 of the second polarity changes in the second polarity duration.

As shown in FIG. 3A, the electrical resistance Rx increases as the absolute value of the first current value Ic1 is increased. As shown in FIG. 3B, the electrical resistance Rx increases as the absolute value of the second current value Ic2 is increased. For example, the increase of the electrical resistance Rx is based on the change of the orientation of the magnetization of the first counter magnetic layer 110 that corresponds to the first current value Ic1 or the second current value Ic2.

When the characteristic illustrated in FIG. 3A and the characteristic corresponding to FIG. 3B are temporally overlaid, the electrical resistance Rx of the first magnetic element 11E has a substantially even-function characteristic with respect to the first current I1.

For example, it is considered that such a characteristic is based on the orientation of the magnetization of the first magnetic layer 11 reversing due to the pulse of the first pulse current value Ip1 and the pulse of the second pulse current value Ip2. For example, the magnetization of the first magnetic layer 11 becomes one of the "+X orientation" or the "−X orientation" due to the pulse of the first pulse current value Ip1. For example, the magnetization of the first magnetic layer 11 becomes the other of the "+X orientation" or the "−X orientation" due to the pulse of the second pulse current value Ip2. On the other hand, for example, when there is substantially no external magnetic field, the magnetization of the first counter magnetic layer 110 is along the Y-axis direction. The change of the electrical resistance Rx illustrated in FIGS. 3A and 3B is obtained by the orientation of the magnetization of the first magnetic layer 11 changing between the first polarity duration and the second polarity duration.

An example of an electrical resistance Rex when an external magnetic field is applied to the first magnetic element 11E when the first current I1 such as that of FIG. 2B is supplied to the first corresponding portion 21 will now be described.

Figure 4A:
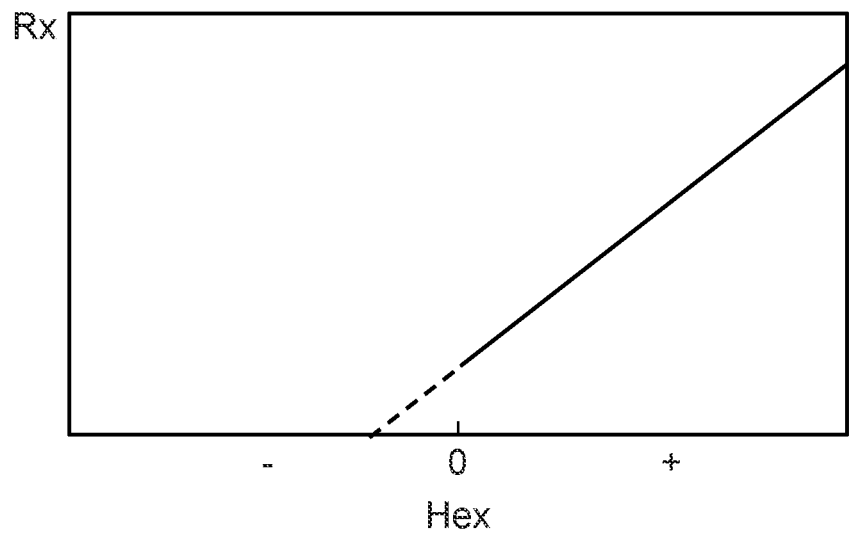
FIGS. 4A and 4B are schematic views illustrating characteristics of the magnetic sensor according to the first embodiment.
Figure 4B:
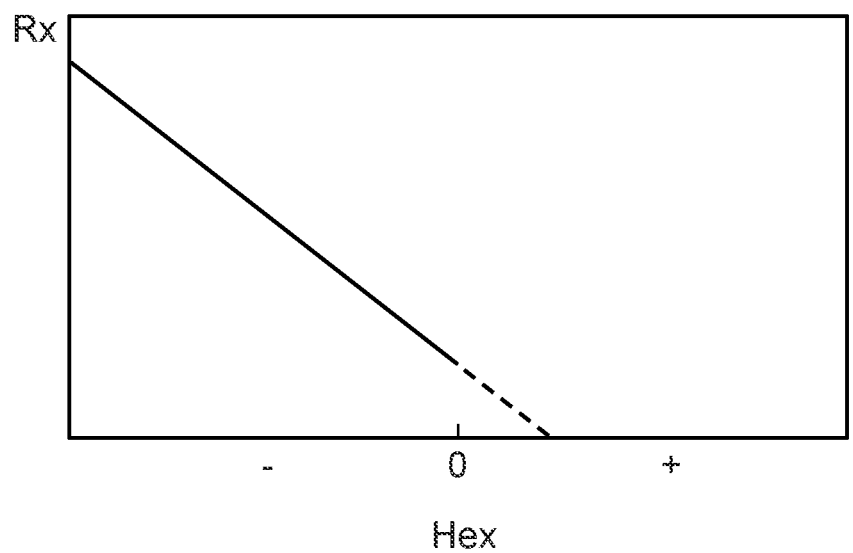

FIGS. 4A and 4B are schematic views illustrating characteristics of the magnetic sensor according to the first embodiment.

In FIGS. 4A and 4B, the horizontal axis is the intensity of an external magnetic field Hex. The external magnetic field Hex includes an X-axis direction component. The vertical axis is the electrical resistance Rx of the first magnetic element 11E. In FIGS. 4A and 4B, the first current value Ic1 or the second current value Ic2 is constant. FIG. 4A corresponds to the first polarity duration. FIG. 4B corresponds to the second polarity duration.

As shown in FIG. 4A, the electrical resistance Rx increases as the absolute value of the external magnetic field Hex of the first polarity (a first orientation) is increased. As shown in FIG. 4B, the electrical resistance Rx increases as the absolute value of the external magnetic field Hex of the second polarity (a second orientation) is increased. For example, the increase of the electrical resistance Rx is based on the change of the orientation of the magnetization of the first counter magnetic layer 110 that corresponds to the external magnetic field Hex.

When the characteristic illustrated in FIG. 4A and the characteristic corresponding to FIG. 4B are temporally overlaid, the electrical resistance Rx of the first magnetic element 11E has a substantially even-function characteristic with respect to the external magnetic field Hex.

It is considered that such a characteristic is caused by, for example, the orientation of the magnetization of the first magnetic layer 11 reversing due to the first and second polarity durations.

Thus, according to the embodiment, the electrical resistance Rx of the first magnetic element 11E that is temporally superimposed has a substantially even-function characteristic with respect to the first current I1 and the external magnetic field Hex.

Figure 5:
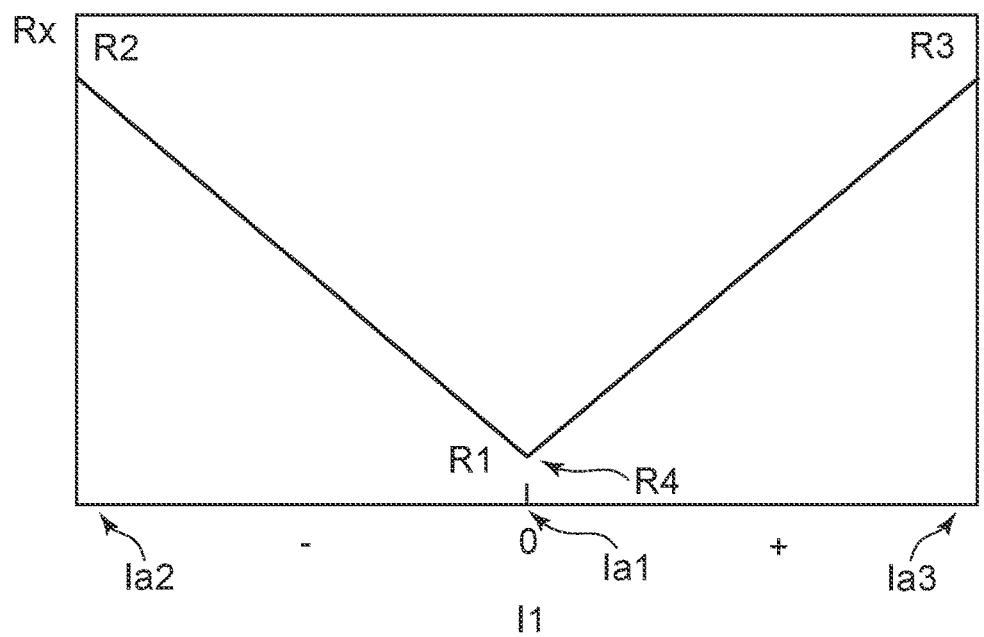
FIG. 5 is a schematic view illustrating a characteristic of the magnetic sensor according to the first embodiment.

FIG. 5 is a schematic view illustrating a characteristic of the magnetic sensor according to the first embodiment.

FIG. 5 illustrates the characteristic when the first polarity duration and the second polarity duration are temporally superimposed. The horizontal axis corresponds to the value of the first current I1 flowing in the first corresponding portion 21. The vertical axis is the electrical resistance Rx of the first magnetic element 11E. According to the embodiment as shown in FIGS. 4A and 4B, the electrical resistance Rx that is temporally superimposed has an even-function characteristic with respect to the change of the first current I1.

For example, the electrical resistance Rx of the first magnetic element 11E has a first resistance value R1 when a first-value current Ia1 is supplied to the first corresponding portion 21. The electrical resistance Rx has a second resistance value R2 when a second-value current Ia2 is supplied to the first corresponding portion 21. The electrical resistance Rx has a third resistance value R3 when a third-value current Ia3 is supplied to the first corresponding portion 21. The absolute value of the first-value current Ia1 is less than the absolute value of the second-value current Ia2 and less than the absolute value of the third-value current Ia3. For example, the first-value current Ia1 may be substantially 0. The orientation of the second-value current Ia2 is opposite to the orientation of the third-value current Ia3.

In the example of FIG. 5, the first resistance value R1 is less than the second resistance value R2 and less than the third resistance value R3. The first resistance value R1 is, for example, the minimum value of the electrical resistance. In one example, the electrical resistance Rx has a fourth resistance value R4 when the current does not flow in the first corresponding portion 21. For example, the first resistance value R1 is substantially equal to the fourth resistance value R4 when the current does not flow. For example, the ratio of the absolute value of the difference between the first resistance value R1 and the fourth resistance value R4 to the fourth resistance value R4 is not more than 0.01. The ratio may be not more than 0.001. A substantially even-function characteristic is obtained with respect to the positive and negative current.

Figure 6:
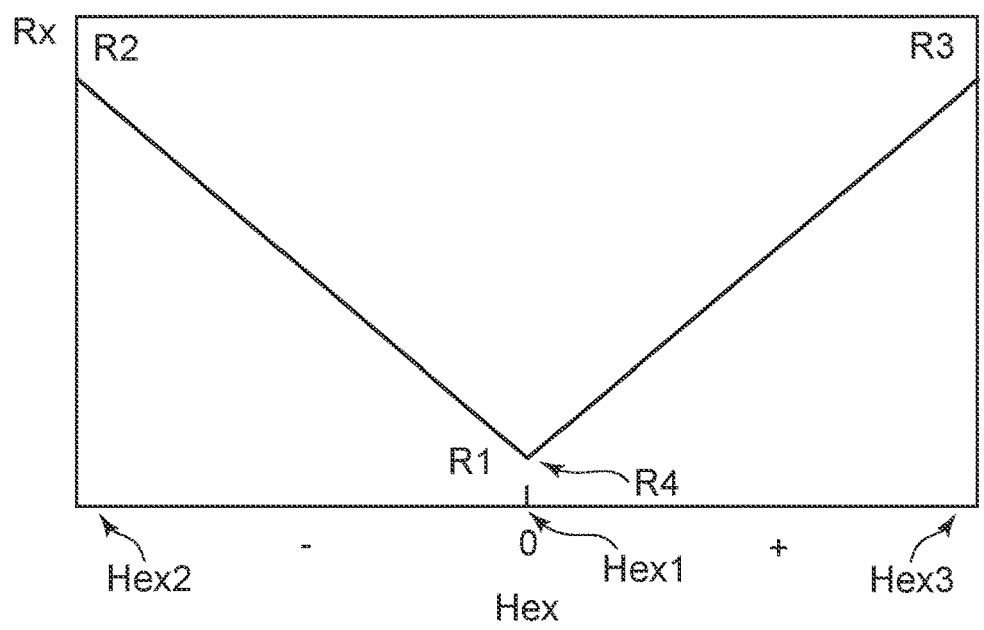
FIG. 6 is a schematic view illustrating a characteristic of the magnetic sensor according to the first embodiment.

FIG. 6 is a schematic view illustrating a characteristic of the magnetic sensor according to the first embodiment.

FIG. 6 illustrates the characteristic when the first polarity duration and the second polarity duration are temporally superimposed. The horizontal axis is the intensity of the external magnetic field Hex applied to the first magnetic element 11E. The vertical axis is the electrical resistance Rx of the first magnetic element 11E. These figures correspond to the R-H characteristic. As shown in FIG. 6, the electrical resistance Rx that is temporally superimposed has an even-function characteristic with respect to the external magnetic field Hex applied to the first magnetic element 11E.

As shown in FIG. 6, the electrical resistance Rx of the first magnetic element 11E has the first resistance value R1 when a first magnetic field Hex1 is applied to the first magnetic element 11E. The electrical resistance Rx has the second resistance value R2 when a second magnetic field Hex2 is applied to the first magnetic element 11E. The electrical resistance Rx has the third resistance value R3 when a third magnetic field Hex3 is applied to the first magnetic element 11E. The absolute value of the first magnetic field Hex1 is less than the absolute value of the second magnetic field Hex2 and less than the absolute value of the third magnetic field Hex3. The orientation of the second magnetic field Hex2 is opposite to the orientation of the third magnetic field Hex3.

In the example of FIG. 6, the first resistance value R1 is less than the second resistance value R2 and less than the third resistance value R3. For example, the electrical resistance Rx has the fourth resistance value R4 when the external magnetic field Hex is not applied to the first magnetic element 11E. The first resistance value R1 is substantially equal to the fourth resistance value R4 when the external magnetic field Hex is not applied. For example, the ratio of the absolute value of the difference between the first resistance value R1 and the fourth resistance value R4 to the fourth resistance value R4 is not more than 0.01. The ratio may be not more than 0.001. A substantially even-function characteristic is obtained with respect to the positive and negative external magnetic field Hex.

Highly-sensitive detection is possible as follows by utilizing such an even-function characteristic.

Figure 7A:
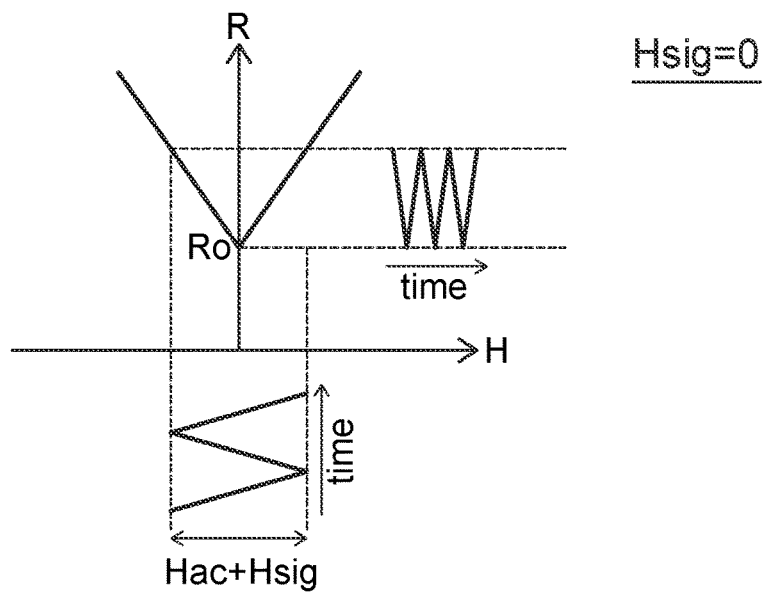
FIGS. 7A to 7C are graphs illustrating characteristics of the magnetic sensor according to the first embodiment.
Figure 7B:
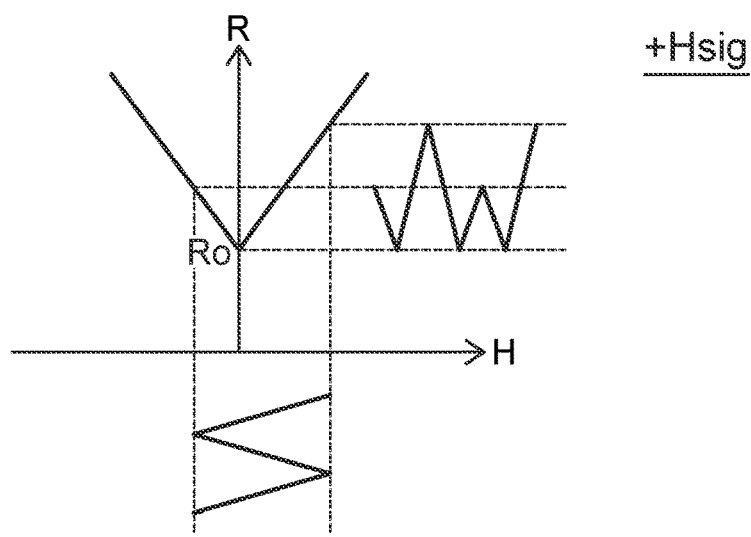
Figure 7C:
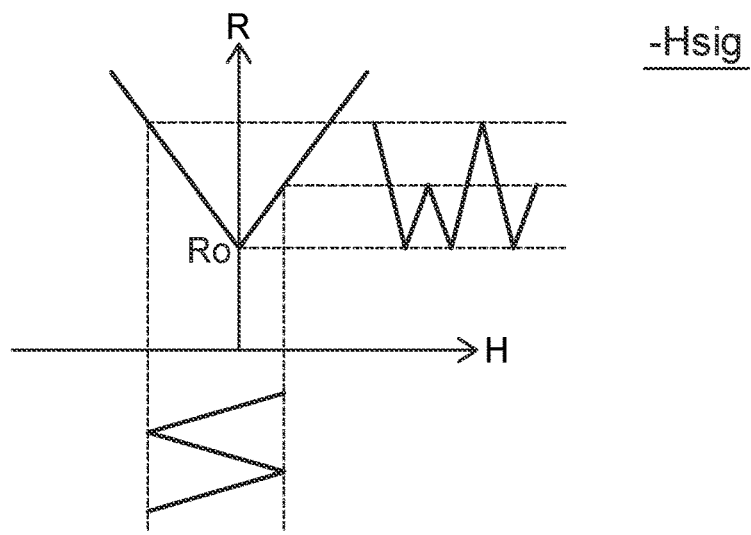

FIGS. 7A to 7C are graphs illustrating characteristics of the magnetic sensor according to the first embodiment.

FIG. 7A shows characteristics when a signal magnetic field Hsig (an external magnetic field Hex) applied to the first magnetic element 11E is 0. FIG. 7B shows characteristics when the signal magnetic field Hsig is positive. FIG. 7C shows characteristics when the signal magnetic field Hsig is negative. These figures show the relationship between a magnetic field H and a resistance R (corresponding to the electrical resistance Rx). The resistance R is the electrical resistance that is temporally superimposed.

As shown in FIG. 7A, when the signal magnetic field Hsig is 0, the resistance R has a characteristic that is symmetric with respect to the positive and negative magnetic field H. When an alternating magnetic field Hac is zero, the resistance R is a low resistance Ro. The change of the resistance R with respect to the alternating magnetic field Hac has the same value between the positive and negative polarities. The period of the change of the resistance R is ½ times the period of the alternating magnetic field Hac. The change of the resistance R substantially does not include the frequency component of the alternating magnetic field Hac.

As shown in FIG. 7B, the characteristic of the resistance R shifts to the positive magnetic field H side when a positive signal magnetic field Hsig is applied. For example, the resistance R becomes high for the alternating magnetic field Hac on the positive side. The resistance R becomes low for the alternating magnetic field Hac on the negative side.

As shown in FIG. 7C, the characteristic of the resistance R shifts to the negative magnetic field H side when a negative signal magnetic field Hsig is applied. For example, the resistance R becomes low for the alternating magnetic field Hac on the positive side. The resistance R becomes high for the alternating magnetic field Hac on the negative side.

Change in the resistance R is different for the positive and negative of the alternating magnetic field Hac when a signal magnetic field Hsig with non-zero magnitude is applied. The period of the change of the resistance R with respect to the positive and negative of the alternating magnetic field Hac is equal to the period of the alternating magnetic field Hac. An output voltage that has an alternating current frequency component corresponding to the signal magnetic field Hsig is generated.

The characteristics described above are obtained in the case where the signal magnetic field Hsig does not temporally change. The case where the signal magnetic field Hsig temporally changes is as follows. The frequency of the signal magnetic field Hsig is taken as a signal frequency fsig. The frequency of the alternating magnetic field Hac is taken as an alternating current frequency fac. In such a case, an output that corresponds to the signal magnetic field Hsig is generated at the frequency of fac±fsig.

In the case where the signal magnetic field Hsig temporally changes, the signal frequency fsig is, for example, not more than 1 kHz. On the other hand, the alternating current frequency fac is sufficiently greater than the signal frequency fsig. For example, the alternating current frequency fac is not less than 10 times the signal frequency fsig.

For example, the signal magnetic field Hsig can be detected with high accuracy by extracting an output voltage having the same period (frequency) component (alternating current frequency component) as the period (the frequency) of the alternating magnetic field Hac. According to the embodiment, the external magnetic field Hex (the signal magnetic field Hsig) that is the detection object can be detected with high sensitivity by utilizing such characteristics.

According to the embodiment, for example, it is favorable for the absolute value of the first pulse current value Ip1 to be not less than 10 times the absolute value of the first current value Ic1 and not less than 10 times the absolute value of the second current value Ic2. It is favorable for the absolute value of the second pulse current value Ip2 to be not less than 10 times the absolute value of the first current value Ic1 and not less than 10 times the absolute value of the second current value Ic2. Thereby, for example, the reversal of the orientation of the magnetization of the first magnetic layer 11 is easier.

According to the embodiment, it is favorable for the first pulse duration Tp1 to be not more than 0.1 times the first duration Ta1 and not more than 0.1 times the second duration Ta2. It is favorable for the second pulse duration Tp2 to be not more than 0.1 times the first duration Ta1 and not more than 0.1 times the second duration Ta2. Thereby, a highly-sensitive magnetic field detection is easier.

According to the embodiment, it is favorable for the first pulse duration Tp1 to be, for example, not less than 1 ns and not more than 1000 ns. It is favorable for the second pulse duration Tp2 to be, for example, not less than 1 ns and not more than 1000 ns. Thereby, a highly-sensitive magnetic field detection is easier.

According to the embodiment, it is favorable for the first duration Ta1 to be, for example, not less than 1 μs and not more than 1 ms. It is favorable for the second duration Ta2 to be, for example, not less than 1 μs and not more than 1 ms. Thereby, a highly-sensitive magnetic field detection is easier. By the signal such as that described above, for example, a highly-sensitive magnetic field detection by extracting an output voltage having the same alternating current frequency component as the alternating magnetic field Hac is easier.

Figure 8A:
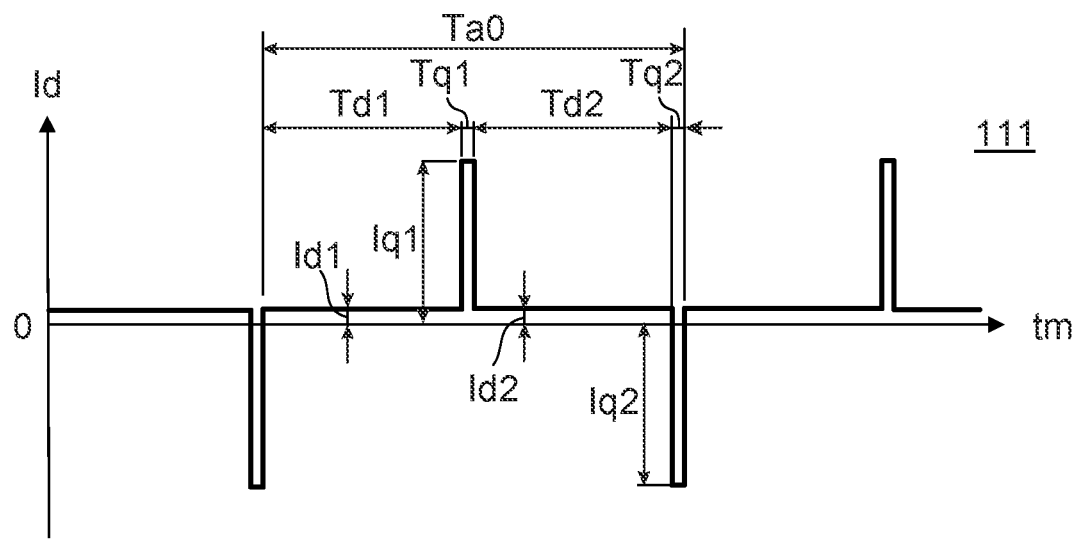
FIGS. 8A and 8B are schematic views illustrating a magnetic sensor according to the first embodiment.
Figure 8B:
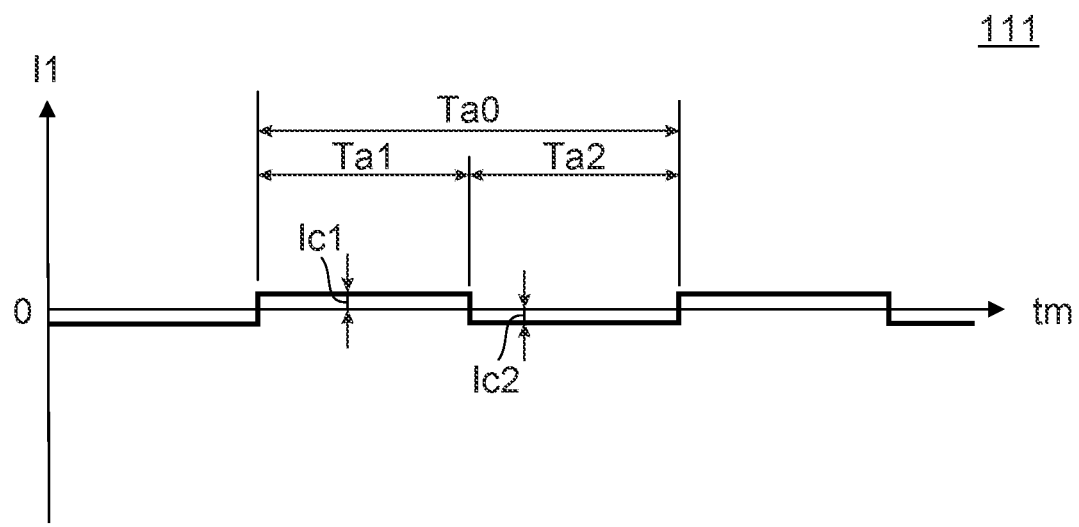

FIGS. 8A and 8B are schematic views illustrating a magnetic sensor according to the first embodiment.

FIGS. 8A and 8B illustrate the element current Id and the first current I1 of the magnetic sensor 111 according to the embodiment. The magnetic sensor 111 also includes the first magnetic element 11E, the conductive member 20, the element current circuit 75, and the first current circuit 71. The operations of the element current circuit 75 and the first current circuit 71 of the magnetic sensor 111 are different from those of the magnetic sensor 110. Otherwise, the configuration of the magnetic sensor 111 may be similar to the configuration of the magnetic sensor 110.

In FIGS. 8A and 8B, the horizontal axis is the time tm. The vertical axis of FIG. 8A is the value of the element current Id. The vertical axis of FIG. 8B is the value of the first current I1.

As shown in FIG. 8B, the first current I1 includes the first duration Ta1 and the second duration Ta2. The first current I1 has the first current value Ic1 of the first polarity in the first duration Ta1. The first current I1 has the second current value Ic2 of the second polarity in the second duration Ta2. The second polarity is different from the first polarity. The first polarity is one of positive or negative. The second polarity is the other of positive or negative. For example, the first duration Ta1 and the second duration Ta2 correspond to the period Ta0 of the alternating current component of the first current I1.

As shown in FIG. 8A, the element current Id includes a first sub-duration Td1, a first sub-pulse duration Tq1, a second sub-duration Td2, and a second sub-pulse duration Tq2. The element current Id has a first element value Id1 of the first polarity in the first sub-duration Td1. The element current Id has a first pulse element value Iq1 of the first polarity in the first sub-pulse duration Tq1. The element current Id has a second element value Id2 of the second polarity in the second sub-duration Td2. The element current Id has a second pulse element value Iq2 of the second polarity in the second sub-pulse duration Tq2.

For example, the first sub-duration Td1 is a portion of the first duration Ta1. The first sub-pulse duration Tq1 is another portion of the first duration Ta1. For example, the second sub-duration Td2 is a portion of the second duration Ta2. The second sub-pulse duration Tq2 is another portion of the second duration Ta2.

The absolute value of the first pulse element value Iq1 is greater than the absolute value of the first element value Id1 and greater than the absolute value of the second element value Id2. The absolute value of the second pulse element value Iq2 is greater than the absolute value of the first element value Id1 and greater than the absolute value of the second element value Id2. The first sub-pulse duration Tq1 is less than the first sub-duration Td1 and less than the second sub-duration Td2. The second sub-pulse duration Tq2 is less than the first sub-duration Td1 and less than the second sub-duration Td2.

For example, the sum of the first sub-duration Td1, the first sub-pulse duration Tq1, the second sub-duration Td2, and the second sub-pulse duration Tq2 corresponds to the period Ta0 of the alternating current component of the first current I1.

By such an element current Id, the electrical resistance Rx of the first magnetic element 11E has a substantially even-function characteristic with respect to the first and second current values Ic1 and Ic2 of the first current I1 when the electrical resistance Rx is temporally superimposed.

In the magnetic sensor 111, the electrical resistance Rx of the first magnetic element 11E has a characteristic similar to the characteristic illustrated in FIGS. 3A and 3B.

The electrical resistance Rx of the first magnetic element 11E increases as the absolute value of the first current value Ic1 of the first current I1 is increased. The electrical resistance Rx increases as the absolute value of the second current value Ic2 of the first current I1 is increased.

In the magnetic sensor 111 as well, the electrical resistance Rx increases as the absolute value of the external magnetic field Hex of the first polarity (the first orientation) is increased. The electrical resistance Rx increases as the absolute value of the external magnetic field Hex of the second polarity (the second orientation) is increased. For example, the electrical resistance Rx that is temporally superimposed has a substantially even-function characteristic with respect to the external magnetic field Hex.

In the magnetic sensor 111 as well, it is considered that such a characteristic is caused by, for example, the orientation of the magnetization of the first magnetic layer 11 reversing due to the first and second polarity durations. In the magnetic sensor 111 as well, for example, the noise can be suppressed by processing the electrical resistance Rx based on the frequency (the period Ta0) of the alternating current component of the first current I1. For example, detection with high sensitivity is possible.

In the magnetic sensor 111, for example, it is favorable for the absolute value of the first pulse element value Iq1 to be not less than 10 times the absolute value of the first element value Id1 and not less than 10 times the absolute value of the second element value Id2. For example, it is favorable for the absolute value of the second pulse element value Iq2 to be not less than 10 times the absolute value of the first element value Id1 and not less than 10 times the absolute value of the second element value Id2. Thereby, the reversal of the orientation of the magnetization of the first magnetic layer 11 is easier.

For example, it is favorable for the first sub-pulse duration Tq1 to be not more than 0.1 times the first sub-duration Td1 and not more than 0.1 times the second sub-duration Td2. For example, it is favorable for the second sub-pulse duration Tq2 to be not more than 0.1 times the first sub-duration Td1 and not more than 0.1 times the second sub-duration Td2. Thereby, a highly-sensitive magnetic field detection is easier.

For example, it is favorable for the first sub-pulse duration Tq1 to be not less than 1 ns and not more than 1000 ns. For example, it is favorable for the second sub-pulse duration Tq2 to be not less than 1 ns and not more than 1000 ns. Thereby, a highly-sensitive magnetic field detection is easier.

For example, it is favorable for the first sub-duration Td1 to be not less than 1 µs and not more than 1 ms. For example, it is favorable for the second sub-duration Td2 to be not less than 1 µs and not more than 1 ms. Thereby, a highly-sensitive magnetic field detection is easier. By a signal such as that described above, for example, a highly-sensitive magnetic field detection by extracting an output voltage having the same alternating current frequency component as the alternating magnetic field Hac is easier.

Second Embodiment

According to a second embodiment, the magnetic sensor includes multiple magnetic elements.

Figure 9:
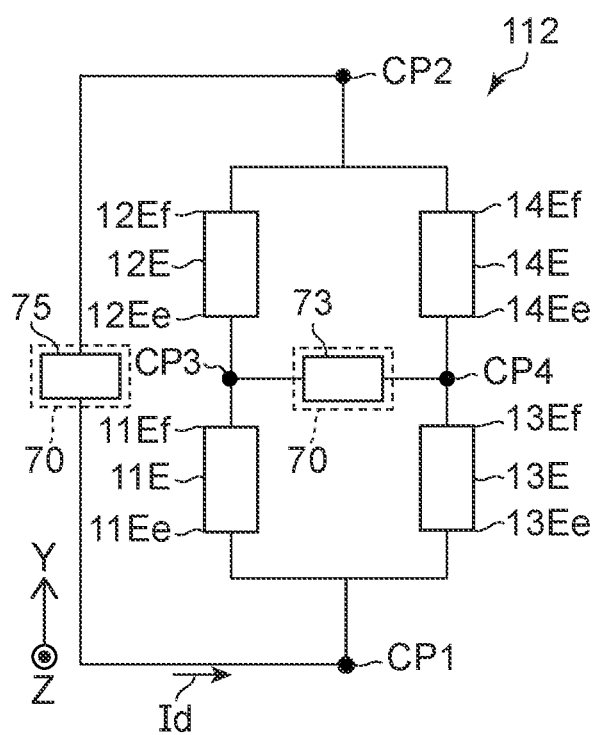
FIG. 9 is a schematic view illustrating a magnetic sensor according to a second embodiment.

FIG. 9 is a schematic view illustrating the magnetic sensor according to the second embodiment.

FIGS. 10A to 10D are schematic views illustrating magnetic sensors according to the second embodiment.

As shown in FIG. 9, the magnetic sensor 112 according to the embodiment includes a second magnetic element 12E, a third magnetic element 13E, and a fourth magnetic element 14E in addition to the first magnetic element 11E. The first magnetic element 11E includes the first end portion 11Ee and the first other-end portion 11Ef. The direction from the first end portion 11Ee toward the first other-end portion 11Ef is along the first direction (e.g., the Y-axis direction). The second magnetic element 12E includes a second end portion 12Ee and a second other-end portion 12Ef. The direction from the second end portion 12Ee toward the second other-end portion 12Ef is along the first direction. The third magnetic element 13E includes a third end portion 13Ee and a third other-end portion 13Ef. The direction from the third end portion 13Ee toward the third other-end portion 13Ef is along the first direction. The fourth magnetic element 14E includes a fourth end portion 14Ee and a fourth other-end portion 14Ef. The direction from the fourth end portion 14Ee toward the fourth other-end portion 14Ef is along the first direction.

Figure 10A:
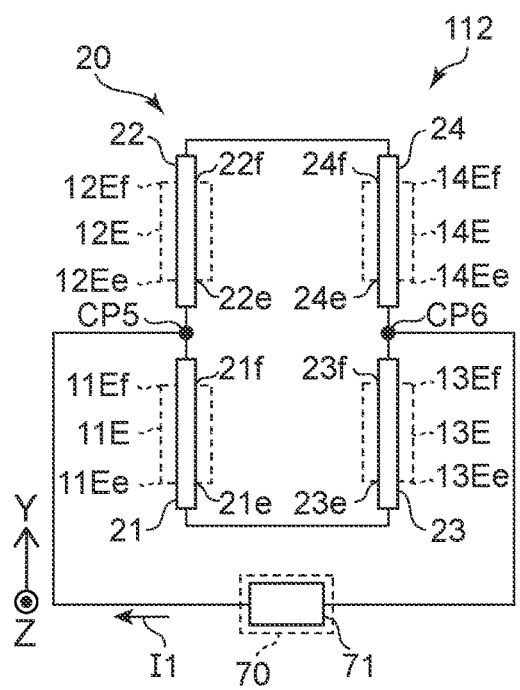
FIGS. 10A to 10D are schematic views illustrating magnetic sensors according to the second embodiment.

In the magnetic sensor 112 as shown in FIG. 10A, the conductive member 20 includes a second corresponding portion 22, a third corresponding portion 23, and a fourth corresponding portion 24 in addition to the first corresponding portion 21. The first corresponding portion 21 is along the first magnetic element 11E. The second corresponding portion 22 is along the second magnetic element 12E. The third corresponding portion 23 is along the third magnetic element 13E. The fourth corresponding portion 24 is along the fourth magnetic element 14E. For example, the first to fourth corresponding portions 21 to 24 respectively overlap the first to fourth magnetic elements 11E to 14E in the Z-axis direction.

As shown in FIG. 1A, for example, the first corresponding portion 21 includes the first portion 21e that corresponds to the first end portion 11Ee, and the first other-portion 21f that corresponds to the first other-end portion 11Ef. The second corresponding portion 22 includes, for example, a second portion 22e that corresponds to the second end portion 12Ee, and a second other-portion 22f that corresponds to the second other-end portion 12Ef. The third corresponding portion 23 includes, for example, a third portion 23e that corresponds to the third end portion 13Ee, and a third other-portion 23f that corresponds to the third other-end portion 13Ef. The fourth corresponding portion 24 includes, for example, a fourth portion 24e that corresponds to the fourth end portion 14Ee, and a fourth other-portion 24f that corresponds to the fourth other-end portion 14Ef.

For example, the first portion 21e overlaps the first end portion 11Ee in the Z-axis direction. For example, the first other-portion 21f overlaps the first other-end portion 11Ef in the Z-axis direction. For example, the second portion 22e overlaps the second end portion 12Ee in the Z-axis direction. For example, the second other-portion 22f overlaps the second other-end portion 12Ef in the Z-axis direction. For example, the third portion 23e overlaps the third end portion 13Ee in the Z-axis direction. For example, the third other-portion 23f overlaps the third other-end portion 13Ef in the Z-axis direction. For example, the fourth portion 24e overlaps the fourth end portion 14Ee in the Z-axis direction. For example, the fourth other-portion 24f overlaps the fourth other-end portion 14Ef in the Z-axis direction.

As shown in FIG. 9, the element current circuit 75 is configured to supply the element current Id to the first magnetic element 11E, the second magnetic element 12E, the third magnetic element 13E, and the fourth magnetic element 14E. The first to fourth magnetic elements 11E to 14E have a bridge connection.

As shown in FIG. 10A, the first current circuit 71 is configured to supply the first current I1 to the first corresponding portion 21, the second corresponding portion 22, the third corresponding portion 23, and the fourth corresponding portion 24.

In the example shown in FIG. 9, the first other-end portion 11Ef is electrically connected with the second end portion 12Ee. The first end portion 11Ee is electrically connected with the third end portion 13Ee. The third other-end portion 13Ef is electrically connected with the fourth end portion 14Ee. The second other-end portion 12Ef is electrically connected with the fourth other-end portion 14Ef.

In the example shown in FIG. 9, the element current circuit 75 is configured to supply the element current Id between a first connection point CP1 and a second connection point CP2, in which the first connection point CP1 is between the first end portion 11Ee and the third end portion 13Ee, and the second connection point CP2 is between the second other-end portion 12Ef and the fourth other-end portion 14Ef.

As shown in FIG. 9, the magnetic sensor 112 may include a detection circuit 73. The detection circuit 73 may be included in the circuit part 70. The detection circuit 73 is configured to detect the change of the potential between a third connection point CP3 and a fourth connection point CP4, in which the third connection point CP3 is between the first other-end portion 11Ef and the second end portion 12Ee, and the fourth connection point CP4 is between the third other-end portion 13Ef and the fourth end portion 14Ee.

In the example shown in FIG. 10A, the first portion 21e is electrically connected with the third portion 23e. The first other-portion 21f is electrically connected with the second portion 22e. The third other-portion 23f is electrically connected with the fourth portion 24e. The second other-portion 22f is electrically connected with the fourth other-portion 24f. The first current circuit 71 is configured to supply the first current I1 between a fifth connection point CP5 and a sixth connection point CP6, in which the fifth connection point CP5 is between the first other-portion 21f and the second portion 22e, and the sixth connection point CP6 is between the third other-portion 23f and the fourth portion 24e.

The magnetic field that is due to the first current I1 flowing through the first corresponding portion 21 is applied to the first magnetic element 11E. The magnetic field that is due to the first current I1 flowing through the second corresponding portion 22 is applied to the second magnetic element 12E. The magnetic field that is due to the first current I1 flowing through the third corresponding portion 23 is applied to the third magnetic element 13E. The magnetic field that is due to the first current I1 flowing through the fourth corresponding portion 24 is applied to the fourth magnetic element 14E.

At one time (a first time) as shown in FIG. 9A, the element current Id flows through the first magnetic element 11E in the orientation from the first end portion 11Ee toward the first other-end portion 11Ef. At the first time, the element current Id flows through the second magnetic element 12E in the orientation from the second end portion 12Ee toward the second other-end portion 12Ef. At the first time, the element current Id flows through the third magnetic element 13E in the orientation from the third end portion 13Ee toward the third other-end portion 13Ef. At the first time, the element current Id flows through the fourth magnetic element 14E in the orientation from the fourth end portion 14Ee toward the fourth other-end portion 14Ef.

At one time (the first time) in the example shown in FIG. 10A, the orientation of the first current I1 is as follows. The first current I1 flows through the first corresponding portion 21 in the orientation from the first other-portion 21f toward the first portion 21e. The first current I1 flows through the second corresponding portion 22 in the orientation from the second portion 22e toward the second other-portion 22f. The first current I1 flows through the third corresponding portion 23 in the orientation from the third portion 23e toward the third other-portion 23f. The first current I1 flows through the fourth corresponding portion 24 in the orientation from the fourth other-portion 24f toward the fourth portion 24e. Thus, at the first time, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e.

For example, at the first time, the relationship between the orientation of the first current I1 flowing through the second corresponding portion 22 at the first time and the orientation of the element current Id flowing through the second magnetic element 12E is opposite to (the opposite phase of) the relationship between the orientation of the first current I1 flowing through the first corresponding portion 21 at the first time and the orientation of the element current Id flowing through the first magnetic element 11E. The relationship between the orientation of the first current I1 flowing through the fourth corresponding portion 24 at the first time and the orientation of the element current Id flowing through the fourth magnetic element 14E is opposite to (the opposite phase of) the relationship between the orientation of the first current I1 flowing through the third corresponding portion 23 at the first time and the orientation of the element current Id flowing through the third magnetic element 13E.

The noise can be further suppressed by such a current flowing in the multiple magnetic elements that have the bridge connection.

In the magnetic sensor 112, for example, the element current Id and the first current I1 have the configuration illustrated in FIGS. 3A and 3B or the configuration illustrated in FIGS. 8A and 8B.

Figure 10B:
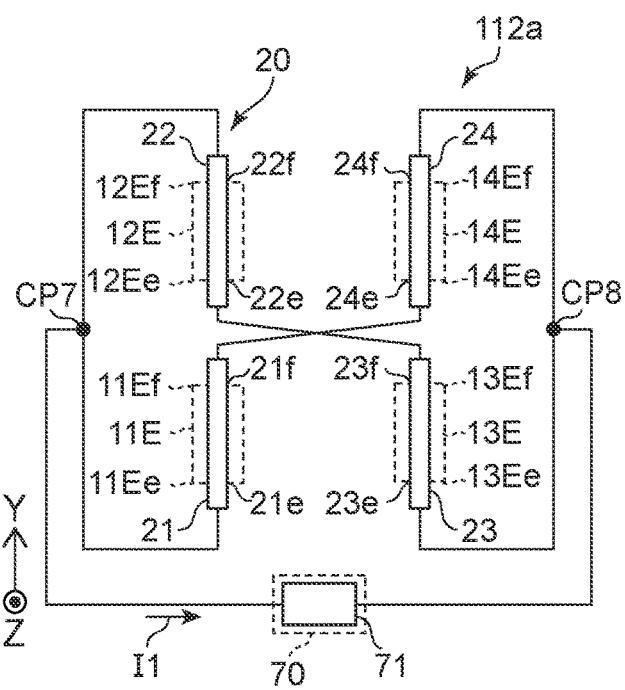
Figure 10C:
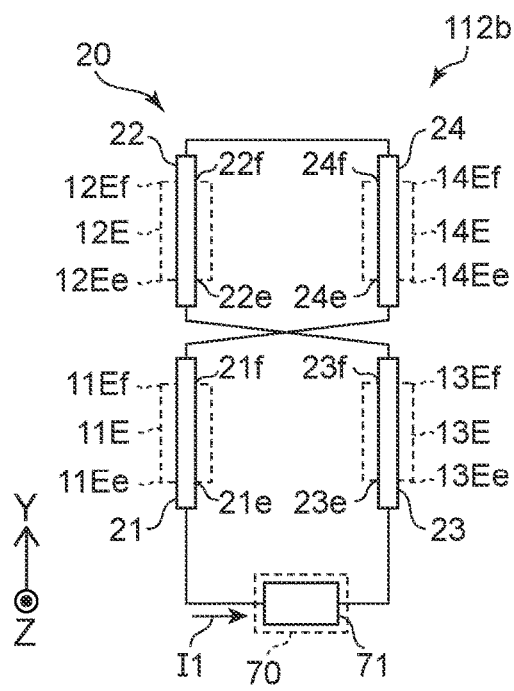
Figure 10D:
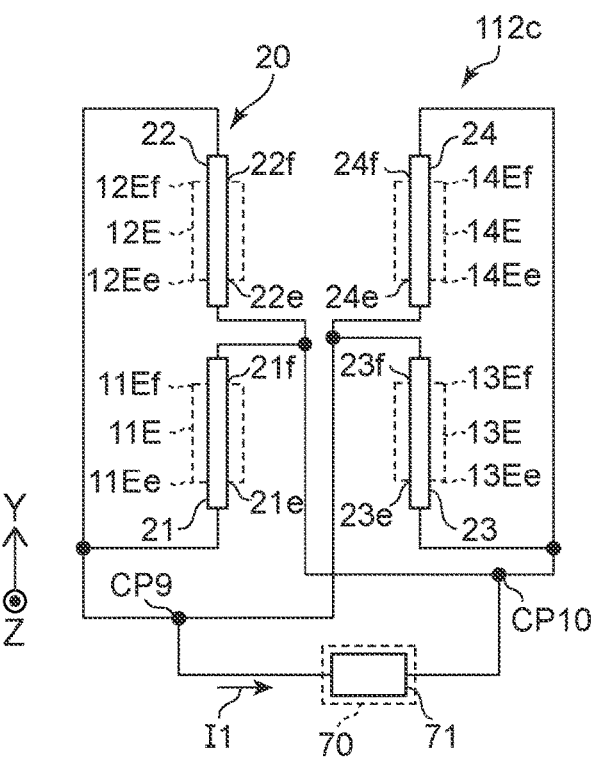

The configurations of magnetic sensors 112a to 112c illustrated in FIGS. 10B to 10D may be combined with the configuration of the magnetic sensor 112 illustrated in FIG. 9.

In the magnetic sensor 112a as shown in FIG. 10B, the first portion 21e is electrically connected with the second other-portion 22f. The first other-portion 21f is electrically connected with the fourth portion 24e. The third portion 23e is electrically connected with the fourth other-portion 24f. The third other-portion 23f is electrically connected with the second portion 22e.

In the magnetic sensor 112a, the first current circuit 71 is configured to supply the first current I1 between a seventh connection point CP7 and an eighth connection point CP8, in which the seventh connection point CP7 is between the first portion 21e and the second other-portion 22f, and the eighth connection point CP8 is between the third portion 23e and the fourth other-portion 24f.

At one time (the first time) in the magnetic sensor 112a, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e. A configuration such as that shown in FIG. 10B may be combined with the configuration of FIG. 9.

In the magnetic sensor 112b as shown in FIG. 10C, the first other-portion 21f is electrically connected with the fourth portion 24e. The third other-portion 23f is electrically connected with the second portion 22e. The second other-portion 22f is electrically connected with the fourth other-portion 24f.

In the magnetic sensor 112b, the first current circuit 71 is configured to supply the first current I1 between the first portion 21e and the third portion 23e.

At one time (the first time) in the magnetic sensor 112b, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e. A configuration such as that shown in FIG. 10C may be combined with the configuration of FIG. 9.

In the magnetic sensor 112c as shown in FIG. 10D, the first portion 21e is electrically connected with the second other-portion 22f, the third other-portion 23f, and the fourth portion 24e. The first other-portion 21f is electrically connected with the second portion 22e, the third portion 23e, and the fourth other-portion 24f.

In the magnetic sensor 112c, the first current circuit 71 is configured to supply the first current I1 that includes the alternating current between a ninth connection point CP9 and a tenth connection point CP10, in which the ninth connection point CP9 is between the first portion 21e, the second other-portion 22f, the third other-portion 23f, and the fourth portion 24e, and the tenth connection point CP10 is between the first other-portion 21f, the second portion 22e, the third portion 23e, and the fourth other-portion 24f.

At one time (the first time) in the magnetic sensor 112c, the first current I1 has the orientation from the first other-portion 21f toward the first portion 21e, the orientation from the second portion 22e toward the second other-portion 22f, the orientation from the third portion 23e toward the third other-portion 23f, and the orientation from the fourth other-portion 24f toward the fourth portion 24e. A configuration such as that shown in FIG. 10D may be combined with the configuration of FIG. 9.

In the magnetic sensors 112 and 112a to 112c as well, it is possible to suppress noise and detect with high sensitivity.

Figure 11A:
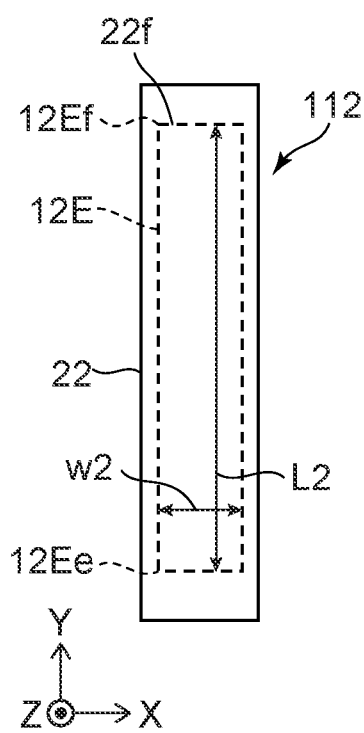
FIGS. 11A to 11C are schematic plan views illustrating the magnetic sensor according to the second embodiment.
Figure 11B:
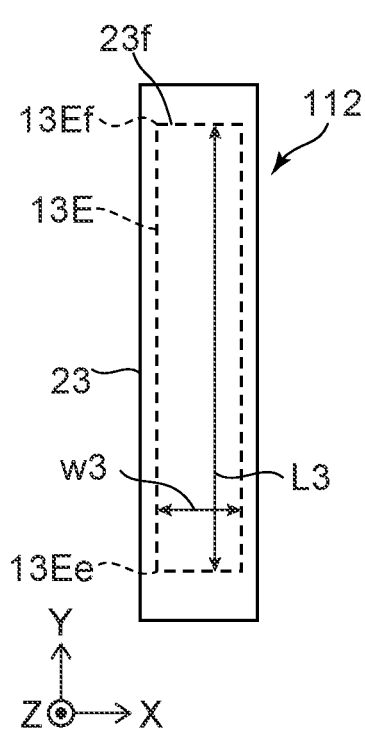
Figure 11C:
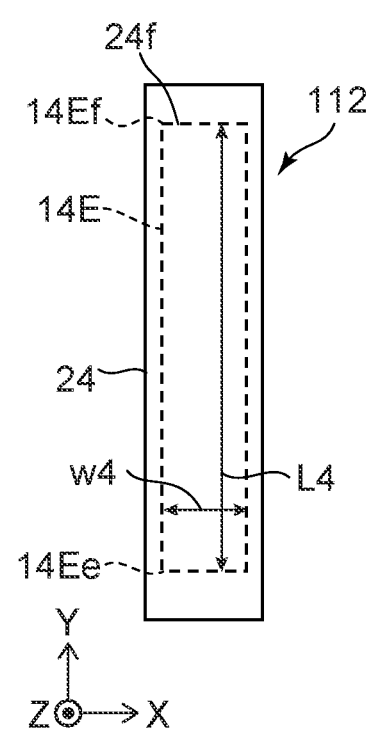

FIGS. 11A to 11C are schematic plan views illustrating the magnetic sensor according to the second embodiment.

As shown in FIG. 11A, the length along the first direction (the Y-axis direction) of the second magnetic element 12E is taken as a second length L2. The length along the second direction of the second magnetic element 12E is taken as a second width w2. The second direction is, for example, the X-axis direction. The second length L2 is greater than the second width w2.

As shown in FIG. 11B, the length along the first direction (the Y-axis direction) of the third magnetic element 13E is taken as a third length L3. The length along the second direction of the third magnetic element 13E is taken as a third width w3. The second direction is, for example, the X-axis direction. The third length L3 is greater than the third width w3.

As shown in FIG. 11C, the length along the first direction (the Y-axis direction) of the fourth magnetic element 14E is taken as a fourth length L4. The length along the second direction of the fourth magnetic element 14E is taken as a fourth width w4. The second direction is, for example, the X-axis direction. The fourth length L4 is greater than the fourth width w4.

FIGS. 12A to 12F are schematic cross-sectional views illustrating the magnetic sensor according to the second embodiment.

Figure 12A:
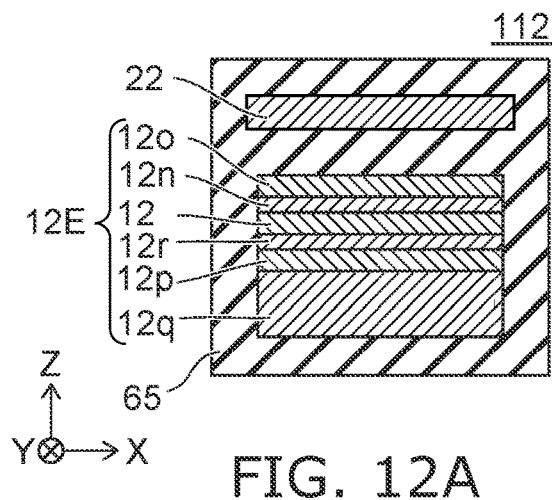
FIGS. 12A to 12F are schematic cross-sectional views illustrating the magnetic sensor according to the second embodiment.
Figure 12B:
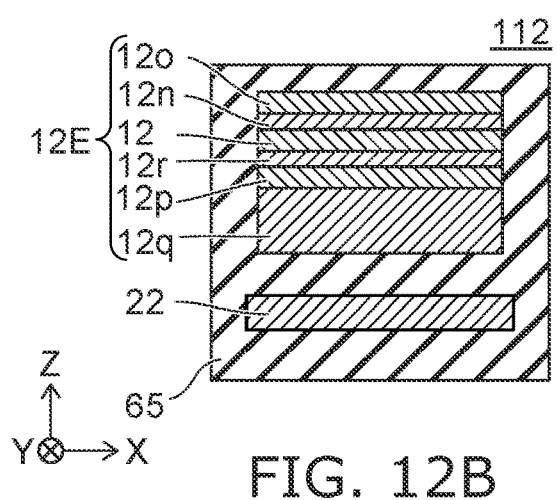

As shown in FIGS. 12A and 12B, for example, the second magnetic element 12E includes a second magnetic layer 12, a second counter magnetic layer 12o, and a second nonmagnetic layer 12n. The second nonmagnetic layer 12n is located between the second magnetic layer 12 and the second counter magnetic layer 12o. The second magnetic element 12E may include a second layer 12q. The second magnetic layer 12 is between the second layer 12q and the second counter magnetic layer 12o. The second magnetic element 12E may include an intermediate magnetic layer 12p and an intermediate nonmagnetic layer 12r. The intermediate magnetic layer 12p is between the second layer 12q and the second magnetic layer 12. The intermediate nonmagnetic layer 12r is between the intermediate magnetic layer 12p and the second magnetic layer 12. For example, the direction from the second magnetic element 12E toward the second corresponding portion 22 is along the third direction (e.g., the Z-axis direction).

Figure 12C:
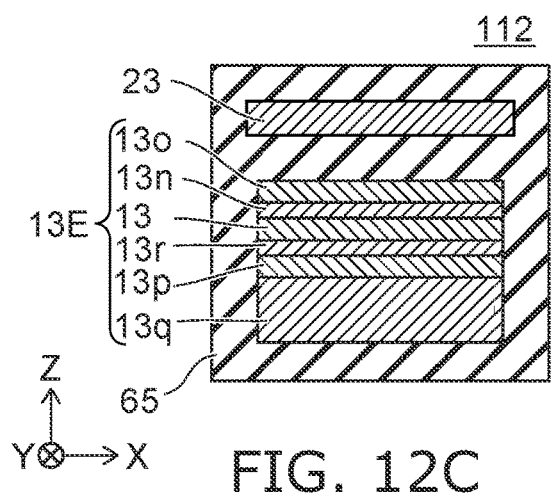
Figure 12D:
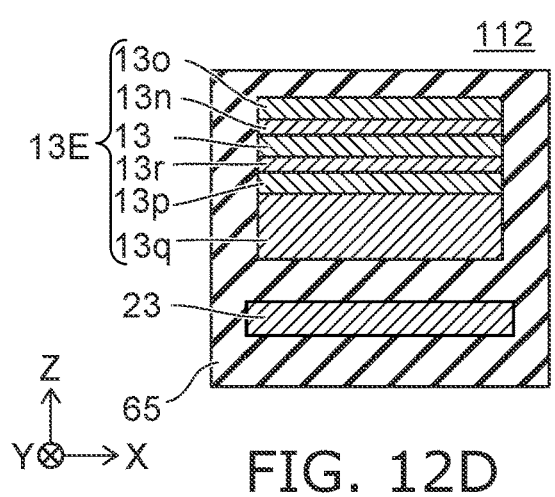

As shown in FIGS. 12C and 12D, for example, the third magnetic element 13E includes a third magnetic layer 13, a third counter magnetic layer 13o, and a third nonmagnetic layer 13n. The third nonmagnetic layer 13n is located between the third magnetic layer 13 and the third counter magnetic layer 13o. The third magnetic element 13E may include a third layer 13q. The third magnetic layer 13 is between the third layer 13q and the third counter magnetic layer 13o. The third magnetic element 13E may include an intermediate magnetic layer 13p and an intermediate nonmagnetic layer 13r. The intermediate magnetic layer 13p is between the third layer 13q and the third magnetic layer 13. The intermediate nonmagnetic layer 13r is between the intermediate magnetic layer 13p and the third magnetic layer 13. For example, the direction from the third magnetic element 13E toward the third corresponding portion 23 is along the third direction (e.g., the Z-axis direction).

Figure 12E:
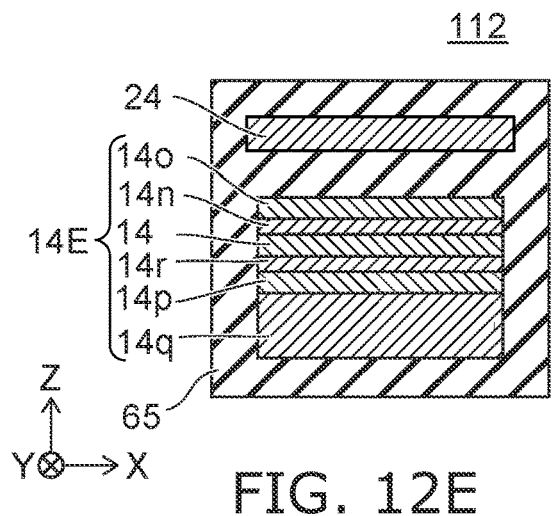
Figure 12F:
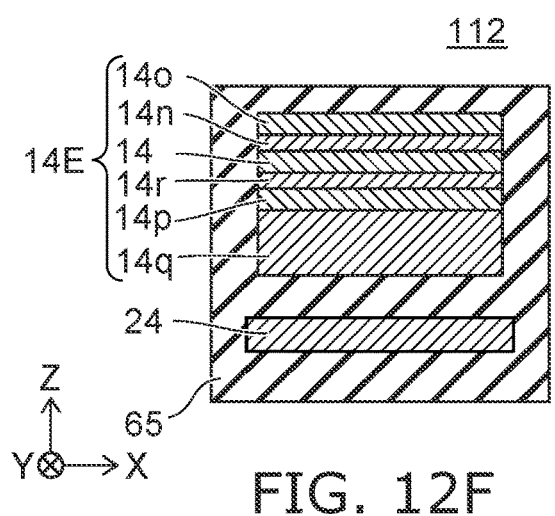

As shown in FIGS. 12E and 12F, for example, the fourth magnetic element 14E includes a fourth magnetic layer 14, a fourth counter magnetic layer 14o, and a fourth nonmagnetic layer 14n. The fourth nonmagnetic layer 14n is located between the fourth magnetic layer 14 and the fourth counter magnetic layer 14o. The fourth magnetic element 14E may include a fourth layer 14q. The fourth magnetic layer 14 is between the fourth layer 14q and the fourth counter magnetic layer 14o. The fourth magnetic element 14E may include an intermediate magnetic layer 14p and an intermediate nonmagnetic layer 14r. The intermediate magnetic layer 14p is between the fourth layer 14q and the fourth magnetic layer 14. The intermediate nonmagnetic layer 14r is between the intermediate magnetic layer 14p and the fourth magnetic layer 14. For example, the direction from the fourth magnetic element 14E toward the fourth corresponding portion 24 is along the third direction (e.g., the Z-axis direction).

The second layer 12q, the third layer 13q, and the fourth layer 14q include, for example, at least one selected from the group consisting of IrMn and PtMn. In one example, the second nonmagnetic layer 12n, the third nonmagnetic layer 13n, and the fourth nonmagnetic layer 14n include at least one selected from the group consisting of Cu, Au, and Ag. The intermediate nonmagnetic layers 12r, 13r, and 14r include, for example, Ru.

FIGS. 13A and 13B are schematic plan views illustrating a magnetic sensor according to the second embodiment.

As shown in FIG. 13A, the magnetic sensor 113 according to the embodiment includes the first magnetic element 11E, the second magnetic element 12E, a first resistance element 11R, and a second resistance element 12R. Otherwise, the configuration of the magnetic sensor 113 may be, for example, the same as the magnetic sensor 110, etc.

The first magnetic element 11E includes the first end portion 11Ee and the first other-end portion 11Ef. The direction from the first end portion 11Ee toward the first other-end portion 11Ef is along the first direction (e.g., the Y-axis direction). The second magnetic element 12E includes the second end portion 12Ee and the second other-end portion 12Ef. The direction from the second end portion 12Ee toward the second other-end portion 12Ef is along the first direction. The first resistance element 11R includes the third end portion 13Ee and the third other-end portion 13Ef. The direction from the third end portion 13Ee toward the third other-end portion 13Ef is along the first direction. The second resistance element 12R includes the fourth end portion 14Ee and the fourth other-end portion 14Ef. The direction from the fourth end portion 14Ee toward the fourth other-end portion 14Ef is along the first direction.

The conductive member 20 includes the first corresponding portion 21 and the second corresponding portion 22. The first corresponding portion 21 is along the first magnetic element 11E. The second corresponding portion 22 is along the second magnetic element 12E.

The first corresponding portion 21 includes the first portion 21e that corresponds to the first end portion 11Ee, and the first other-portion 21f that corresponds to the first other-end portion 11Ef. The second corresponding portion 22 includes the second portion 22e that corresponds to the second end portion 12Ee, and the second other-portion 22f that corresponds to the second other-end portion 12Ef. The element current circuit 75 is configured to supply the element current Id to the first magnetic element 11E, the second magnetic element 12E, the first resistance element 11R, and the second resistance element 12R. The first current circuit 71 is configured to supply the first current I1 to the first and second corresponding portions 21 and 22.

In the magnetic sensor 113, the first end portion 11Ee of the first magnetic element 11E is electrically connected with the third end portion 13Ee of the first resistance element 11R. The first other-end portion 11Ef of the first magnetic element 11E is electrically connected with the second end portion 12Ee of the second magnetic element 12E. The third other-end portion 13Ef of the first resistance element 11R is electrically connected with the fourth end portion 14Ee of the second resistance element 12R. The second other-end portion 12Ef of the second magnetic element 12E is electrically connected with the fourth other-end portion 14Ef of the second resistance element 12R.

The element current circuit 75 is configured to supply the element current Id between the first connection point CP1 and the second connection point CP2, in which the first connection point CP1 is between the first end portion 11Ee of the first magnetic element 11E and the third end portion 13Ee of the first resistance element 11R, and the second connection point CP2 is between the second other-end portion 12Ef of the second magnetic element 12E and the fourth other-end portion 14Ef of the second resistance element 12R.

The detection circuit 73 is configured to detect the change of the potential between the third connection point CP3 and the fourth connection point CP4, in which the third connection point CP3 is between the first other-end portion 11Ef of the first magnetic element 11E, the second magnetic element 12E, and the second end portion 12Ee, and the fourth connection point CP4 is between the third other-end portion 13Ef of the first resistance element 11R and the fourth end portion 14Ee of the second resistance element 12R.

As shown in FIG. 13B, the first other-portion 21f is electrically connected with the second portion 22e. The first portion 21e is electrically connected with the second other-portion 22f. The first current circuit 71 is configured to supply the first current I1 between the fifth connection point CP5 and the sixth connection point CP6, in which the fifth connection point CP5 is between the first other-portion 21f and the second portion 22e, and the sixth connection point CP6 is between the first portion 21e and the second other-portion 22f. In the magnetic sensor 113 as well, it is possible to suppress noise and detect with high sensitivity.

FIGS. 14A and 14B are schematic plan views illustrating a magnetic sensor according to the second embodiment.

As shown in FIG. 14A, the magnetic sensor 114 according to the embodiment includes the first magnetic element 11E, the second magnetic element 12E, the first resistance element 11R, and the second resistance element 12R. Otherwise, the configuration of the magnetic sensor 114 may be, for example, the same as the magnetic sensor 110, etc.

In the magnetic sensor 114 as shown in FIG. 14A, the first end portion 11Ee of the first magnetic element 11E is electrically connected with the third end portion 13Ee of the first resistance element 11R. The first other-end portion 11Ef of the first magnetic element 11E is electrically connected with the fourth end portion 14Ee of the second resistance element 12R. The third other-end portion 13Ef of the first resistance element 11R is electrically connected with the second end portion 12Ee of the second magnetic element 12E. The fourth other-end portion 14Ef of the second resistance element 12R is electrically connected with the second other-end portion 12Ef of the second magnetic element 12E.

The element current circuit 75 is configured to supply the element current Id between the first connection point CP1 and the second connection point CP2, in which the first connection point CP1 is between the first end portion 11Ee and the third end portion 13Ee, and the second connection point CP2 is between the fourth other-end portion 14Ef and the second other-end portion 12Ef.

The magnetic sensor 114 may include the detection circuit 73. The detection circuit 73 is configured to detect the change of the potential between the third connection point CP3 and the fourth connection point CP4, in which the third connection point CP3 is between the first other-end portion 11Ef and the fourth end portion 14Ee, and the fourth connection point CP4 is between the third other-end portion 13Ef and the second end portion 12Ee.

As shown in FIG. 14B, the first portion 21e of the first corresponding portion 21 is electrically connected with the second portion 22e of the second corresponding portion 22. The first other-portion 21f of the first corresponding portion 21 is electrically connected with the second other-portion 22f of the second corresponding portion 22.

The first current circuit 71 is configured to supply the first current I1 between the fifth connection point CP5 and the sixth connection point CP6, in which the fifth connection point CP5 is between the first other-portion 21f and the second other-portion 22f, and the sixth connection point CP6 is between the first portion 21e and the second portion 22e.

According to the second embodiment, the configuration of FIGS. 2A and 2B or the configuration of FIGS. 8A and 8B is applicable to the element current Id and the first current I1.

According to the first and second embodiments, the absolute value of the first current value Ic1 and the absolute value of the second current value Ic2 may change with respect to the time tm.

According to the first and second embodiments, for example, the absolute value of the pulse of the first polarity may be controlled to be different from the absolute value of the pulse of the second polarity. According to the first and second embodiments, for example, the direct current component of the first current I1 may be controlled. For example, the absolute value of the first current value Ic1 may be controlled to be different from the absolute value of the second current value Ic2. According to the second embodiment, for example, the absolute value of the first element value Id1 may be controlled to be different from the absolute value of the second element value Id2.

Third Embodiment

A third embodiment relates to an inspection device. As described below, the inspection device may include a diagnostic device.

Figure 15:
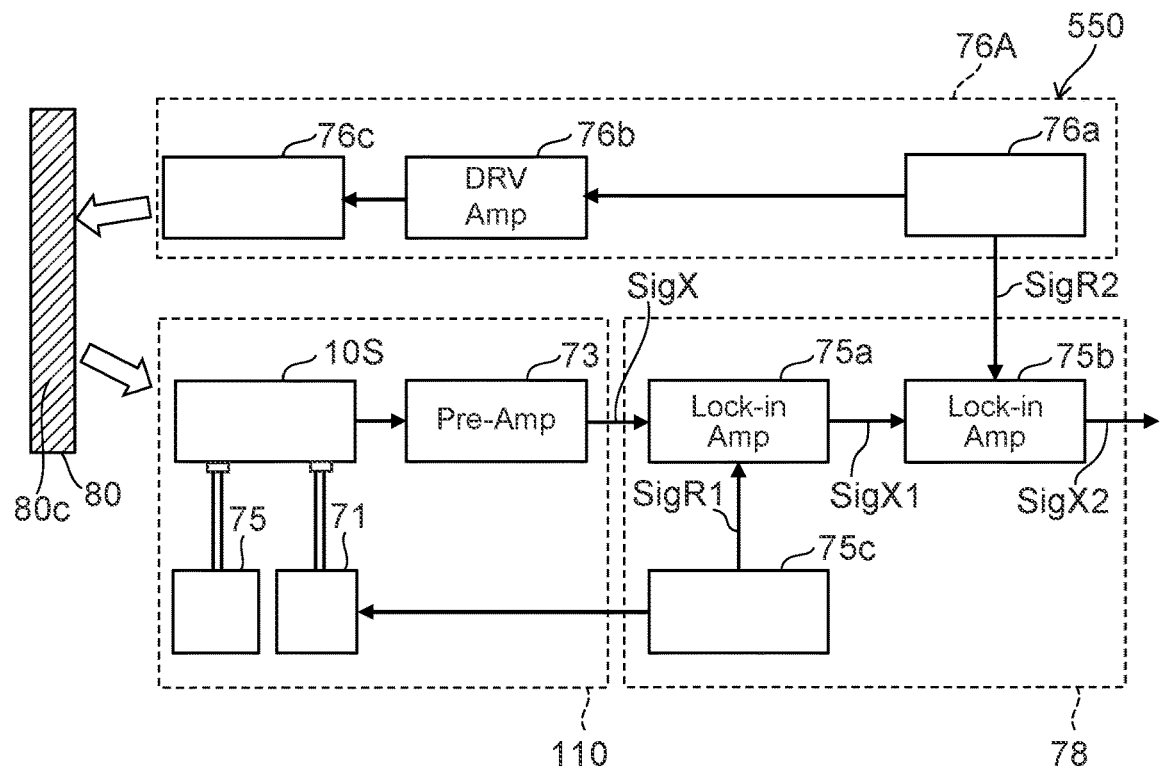
FIG. 15 is a schematic view illustrating an inspection device according to a third embodiment.

FIG. 15 is a schematic view illustrating the inspection device according to the third embodiment.

As shown in FIG. 15, the inspection device 550 according to the embodiment includes a processor 78 and the magnetic sensor (in the example of FIG. 15, the magnetic sensor 110) according to the embodiment. The processor 78 processes an output signal SigX obtained from the magnetic sensor 110. In the example, the processor 78 includes a sensor control circuit part 75c, a first lock-in amplifier 75a, and a second lock-in amplifier 75b. For example, the first current circuit 71 is controlled by the sensor control circuit part 75c; and the first current I1 that includes the alternating current component is supplied from the first current circuit 71 to a sensor part 10S. The frequency of the alternating current component of the first current I1 is, for example, not more than 100 kHz. The element current Id is supplied from the element current circuit 75 to the sensor part 10S. The sensor part 10S includes, for example, at least one magnetic element. The change of the potential of the sensor part 10S is detected by the detection circuit 73. For example, the output of the detection circuit 73 is the output signal SigX.

In the example, the inspection device 550 includes a magnetic field application part 76A. The magnetic field application part 76A is configured to apply a magnetic field to a detection object 80. The detection object 80 is, for example, the inspection object. The detection object 80 includes at least an inspection conductive member 80c such as a metal, etc. For example, an eddy current is generated in the inspection conductive member 80c when the magnetic field due to the magnetic field application part 76A is applied to the inspection conductive member 80c. The state of the eddy current changes when there is a flaw or the like in the inspection conductive member 80c. The state (e.g., the flaw, etc.) of the inspection conductive member 80c can be inspected by the magnetic sensor (e.g., the magnetic sensor 110, etc.) detecting the magnetic field due to the eddy current. The magnetic field application part 76A is, for example, an eddy current generator.

In the example, the magnetic field application part 76A includes an application control circuit part 76a, a drive amplifier 76b, and a coil 76c. A current is supplied to the drive amplifier 76b by the control by the application control circuit part 76a. The current is, for example, an alternating current. The frequency of the current is, for example, an eddy current excitation frequency. The eddy current excitation frequency is, for example, not less than 10 Hz and not more than 100 kHz. The eddy current excitation frequency may be, for example, less than 100 kHz.

For example, information (which may be, for example, a signal) that relates to the frequency of the alternating current component of the first current I1 is supplied from the sensor control circuit part 75c to the first lock-in amplifier 75a as a reference wave (a reference signal). The output of the first lock-in amplifier 75a is supplied to the second lock-in amplifier 75b. Information (which may be, for example, a signal) that relates to the eddy current excitation frequency is supplied from the application control circuit part 76a to the second lock-in amplifier 75b as a reference wave (a reference signal). The second lock-in amplifier 75b is configured to output a signal component corresponding to the eddy current excitation frequency.

Thus, for example, the processor 78 includes the first lock-in amplifier 75a. The output signal SigX that is obtained from the magnetic sensor 110 and a signal SigR1 that corresponds to the frequency of the alternating current component included in the first current I1 are input to the first lock-in amplifier 75a. The first lock-in amplifier 75a is configured to output an output signal SigX1 that uses the signal SigR1 corresponding to the frequency of the alternating current component included in the first current I1 as a reference wave (a reference signal). By providing the first lock-in amplifier 75a, it is possible to suppress noise and detect with high sensitivity.

The processor 78 may further include the second lock-in amplifier 75b. The output signal SigX1 of the first lock-in amplifier 75a and a signal SigR2 that corresponds to the frequency (the eddy current excitation frequency) of the supply signal (in the example, the magnetic field due to the magnetic field application part 76A) supplied toward the detection object 80 (the inspection object) are input to the second lock-in amplifier 75b. The second lock-in amplifier 75b is configured to output an output signal SigX2 that uses the signal SigR2 corresponding to the frequency of the supply signal supplied toward the detection object 80 (the inspection object) as a reference wave (a reference signal). By providing the second lock-in amplifier 75b, it is possible to further suppress noise and detect with even higher sensitivity.

An abnormality such as a flaw or the like of the inspection conductive member 80c of the detection object 80 can be inspected by the inspection device 550.

Figure 16:
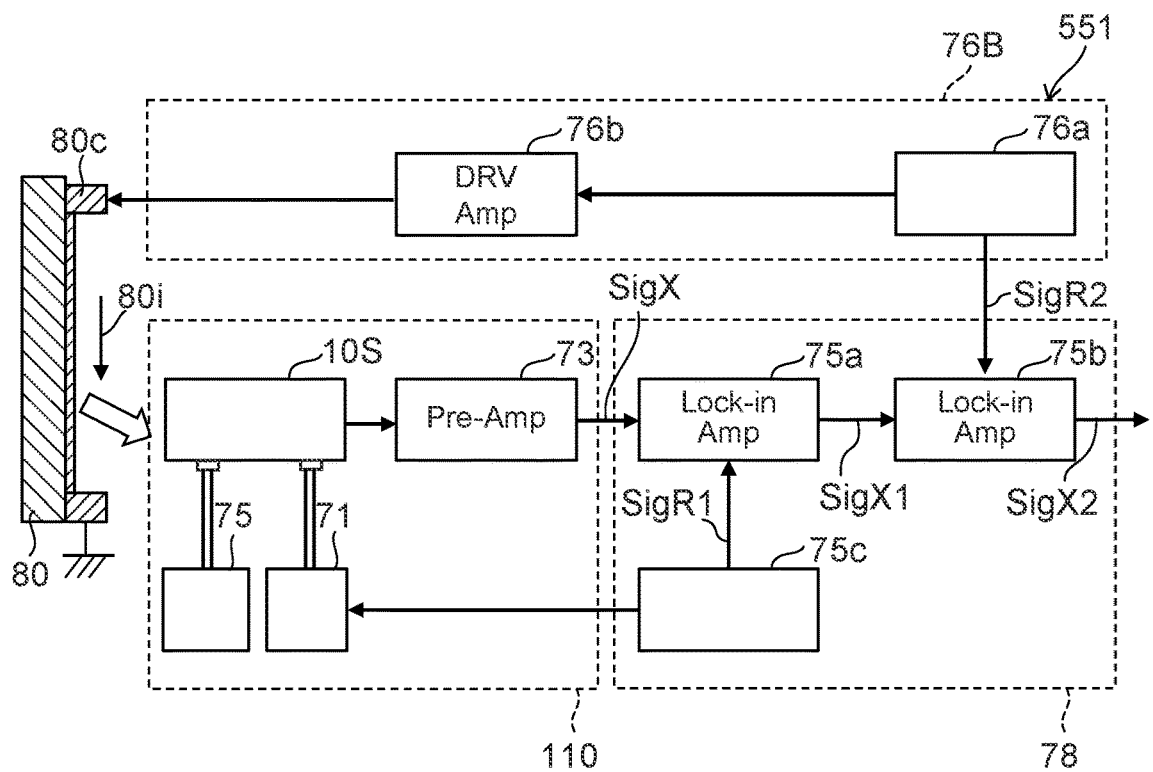
FIG. 16 is a schematic view illustrating an inspection device according to the third embodiment.

FIG. 16 is a schematic view illustrating an inspection device according to the third embodiment.

As shown in FIG. 16, the inspection device 551 according to the embodiment includes the processor 78 and the magnetic sensor (e.g., the magnetic sensor 110) according to the embodiment. The configurations of the magnetic sensor and the processor 78 of the inspection device 551 may be similar to those of the inspection device 550. In the example, the inspection device 551 includes a detection object driver 76B. The detection object driver 76B is configured to supply a current to the inspection conductive member 80c included in the detection object 80. The inspection conductive member 80c is, for example, wiring included in the detection object 80. A magnetic field that is due to a current 80i flowing in the inspection conductive member 80c is detected by the magnetic sensor 110. The inspection conductive member 80c can be inspected based on an abnormality due to the detection result of the magnetic sensor 110. The detection object 80 may be, for example, an electronic device such as a semiconductor device, etc. The detection object 80 may be, for example, a battery, etc.

In the example, the detection object driver 76B includes the application control circuit part 76a and the drive amplifier 76b. The drive amplifier 76b is controlled by the application control circuit part 76a; and a current is supplied from the drive amplifier 76b to the inspection conductive member 80c. The current is, for example, an alternating current. For example, the alternating current is supplied to the inspection conductive member 80c. The frequency of the alternating current is, for example, not less than 10 Hz and not more than 100 kHz. The frequency may be, for example, less than 100 kHz. In the example as well, for example, by providing the first lock-in amplifier 75a and the second lock-in amplifier 75b, it is possible to suppress noise and detect with high sensitivity. In one example of the inspection device 551, multiple magnetic sensors (e.g., the multiple magnetic sensors 110) may be provided. The multiple magnetic sensors are, for example, a sensor array. The inspection conductive member 80c can be inspected in a short period of time by the sensor array. In one example of the inspection device 551, the inspection conductive member 80c may be inspected by scanning the magnetic sensor (e.g., the magnetic sensor 110).

Figure 17:
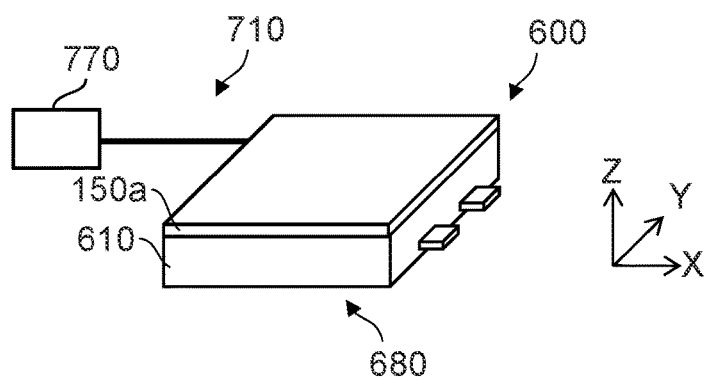
FIG. 17 is a schematic perspective view showing an inspection device according to the third embodiment.

FIG. 17 is a schematic perspective view showing an inspection device according to the third embodiment.

As shown in FIG. 17, the inspection device 710 according to the embodiment includes a magnetic sensor 150a and a processor 770. The magnetic sensor 150a may be the magnetic sensor according to one of the first or second embodiment or a modification of the magnetic sensor. The processor 770 processes an output signal obtained from the magnetic sensor 150a. The processor 770 may perform a comparison between a reference value and the signal obtained from the magnetic sensor 150a, etc. The processor 770 is configured to output an inspection result based on the processing result.

For example, an inspection object 680 is inspected by the inspection device 710. The inspection object 680 is, for example, an electronic device (including a semiconductor circuit, etc.). The inspection object 680 may be, for example, a battery 610, etc.

For example, the magnetic sensor 150a according to the embodiment may be used together with the battery 610. For example, a battery system 600 includes the battery 610 and the magnetic sensor 150a. The magnetic sensor 150a can detect a magnetic field generated by a current flowing in the battery 610.

Figure 18:
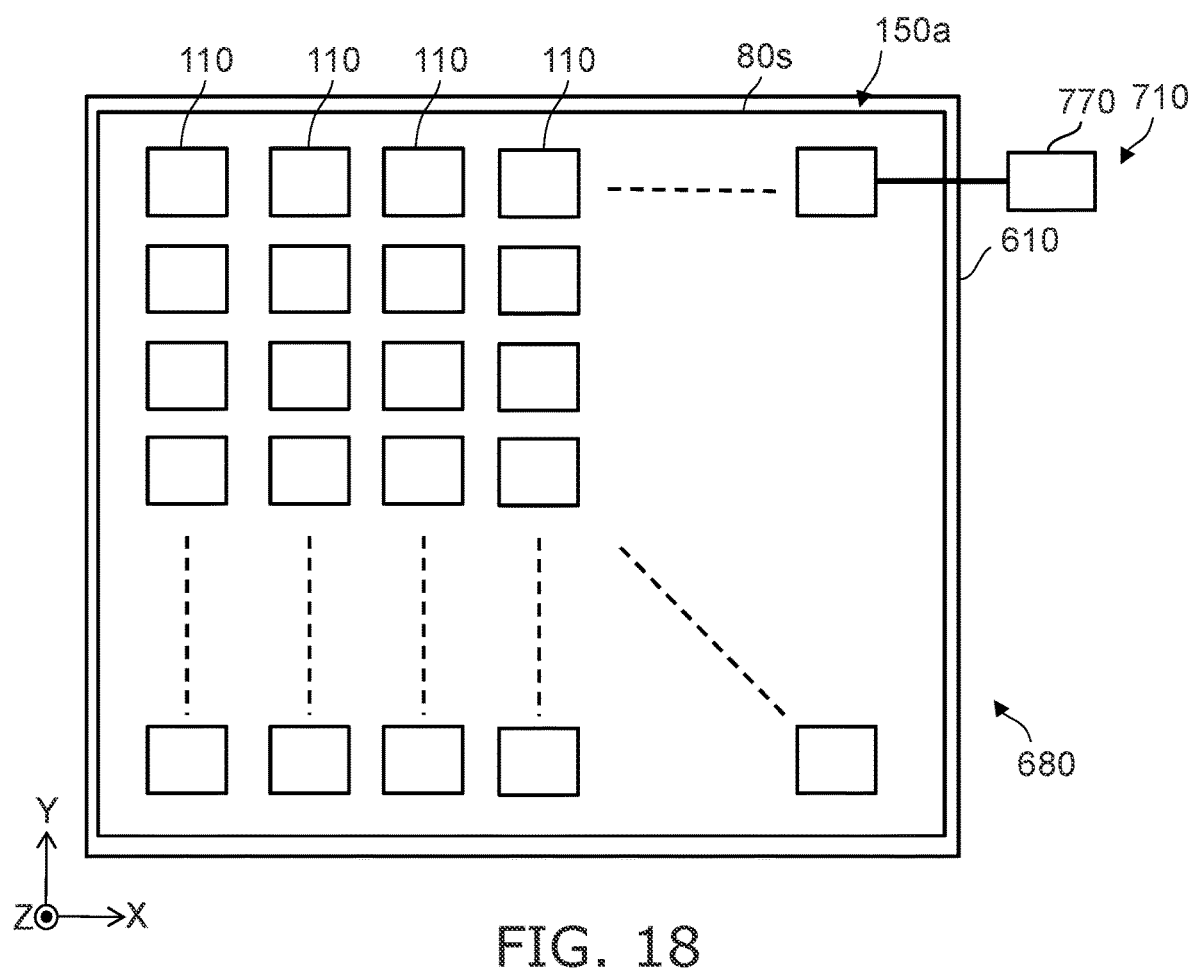
FIG. 18 is a schematic plan view showing the inspection device according to the third embodiment.

FIG. 18 is a schematic plan view showing the inspection device according to the third embodiment.

As shown in FIG. 18, the magnetic sensor 150a includes, for example, multiple magnetic sensors according to the embodiment. In the example, the magnetic sensor 150a includes multiple magnetic sensors (e.g., the magnetic sensor 110, etc.). For example, the multiple magnetic sensors are arranged along two directions (e.g., the X-axis direction and the Y-axis direction). For example, the multiple magnetic sensors 110 are located on a base body.

The magnetic sensor 150a can detect a magnetic field generated by a current flowing in the inspection object 680 (which may be, for example, the battery 610). For example, an abnormal current flows in the battery 610 when the battery 610 approaches an abnormal state. The change of the state of the battery 610 can be known by the magnetic sensor 150a detecting the abnormal current. For example, the entire battery 610 can be inspected in a short period of time by moving the sensor array in two directions while the magnetic sensor 150a is proximate to the battery 610. The magnetic sensor 150a may be used to inspect the battery 610 in the manufacturing process of the battery 610.

Figure 19:
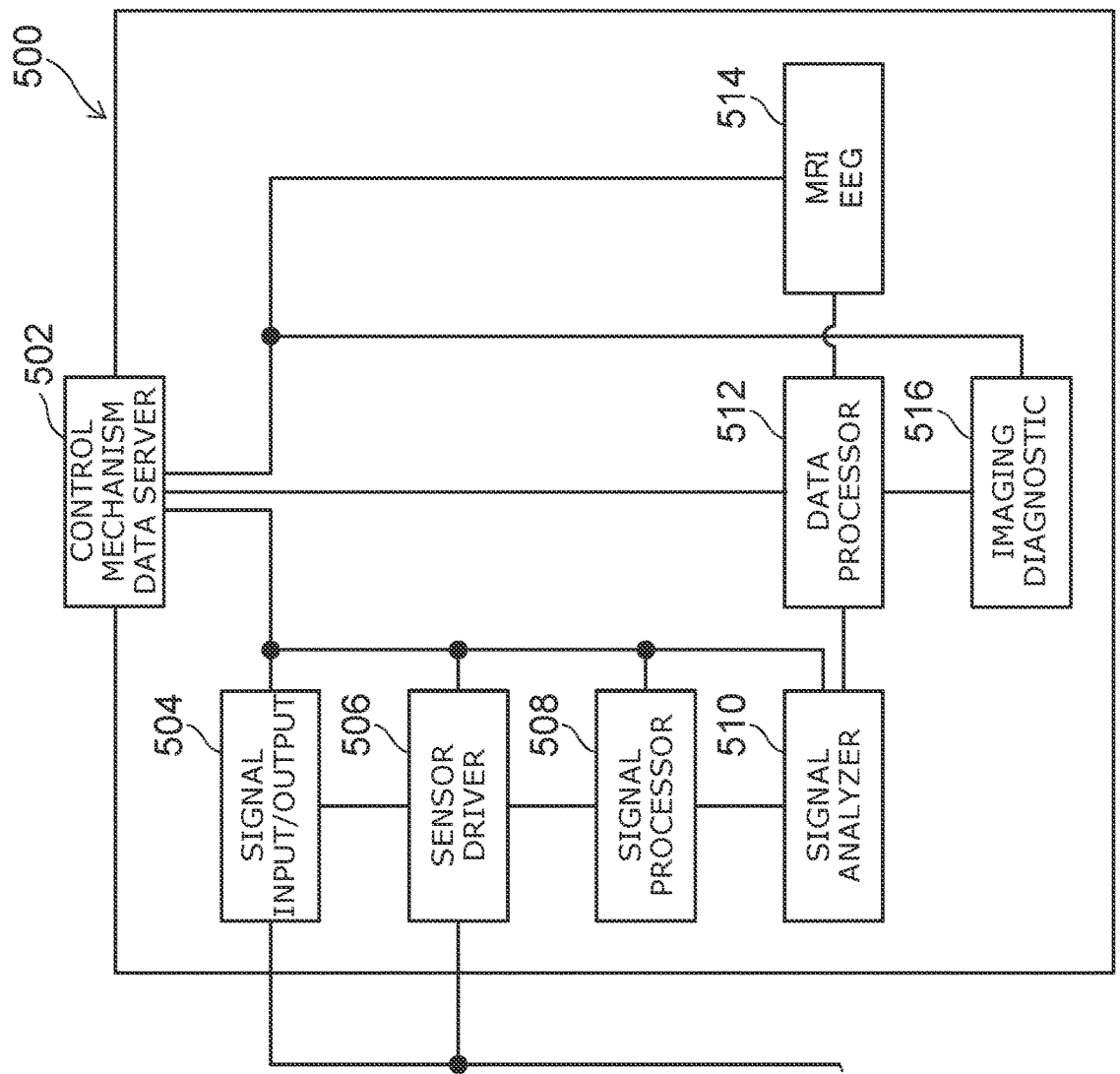
FIG. 19 is a schematic view showing the magnetic sensor and the inspection device according to the third embodiment.
Figure 19:
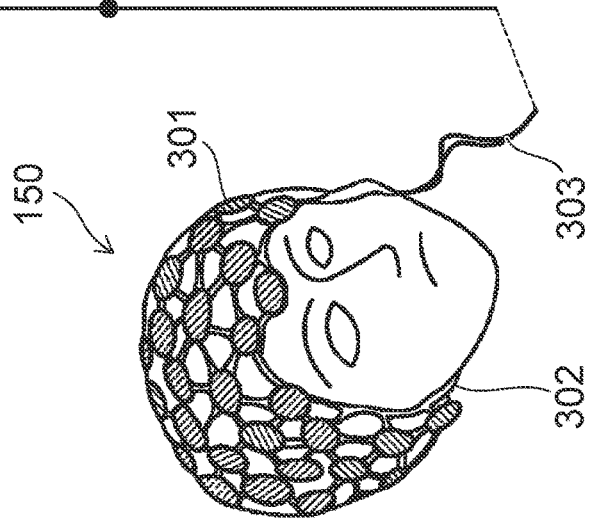

For example, the magnetic sensor according to the embodiment is applicable to the inspection device 710 such as a diagnostic device, etc. FIG. 19 is a schematic view showing the magnetic sensor and the inspection device according to the third embodiment.

As shown in FIG. 19, the diagnostic device 500 is an example of the inspection device 710 and includes the magnetic sensor 150. The magnetic sensor 150 includes the magnetic sensor described in reference to the first or second embodiment or a modification of the magnetic sensor.

In the diagnostic device 500, the magnetic sensor 150 is, for example, a magnetoencephalography device. The magnetoencephalography device detects a magnetic field generated by cranial nerves. When the magnetic sensor 150 is used in a magnetoencephalography device, the size of the magnetic element included in the magnetic sensor 150 is, for example, not less than 1 mm but less than 10 mm. The size is, for example, the length including the MFC.

As shown in FIG. 19, the magnetic sensor 150 (the magnetoencephalography device) is mounted to, for example, the head of a human body. The magnetic sensor 150 (the magnetoencephalography device) includes a sensor part 301. The magnetic sensor 150 (the magnetoencephalography device) may include multiple sensor parts 301. The number of the multiple sensor parts 301 is, for example, about 100 (e.g., not less than 50 and not more than 150). The multiple sensor parts 301 are provided on a flexible base body 302.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 is small compared to the size of a conventional SQUID magnetic sensor. Therefore, the mounting of the multiple sensor parts 301 is easy. The mounting of the multiple sensor parts 301 and the other circuits is easy. The multiple sensor parts 301 and the other sensors can be easily mounted together.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected with a sensor driver 506 and a signal input/output part 504 of the diagnostic device 500. A magnetic field measurement is performed in the sensor part 301 based on electrical power from the sensor driver 506 and a control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography.

For example, signal analysis to match the signal phases is performed in the signal analyzer 510.

The output of the signal analyzer 510 (the data for which the signal analysis is finished) is supplied to a data processor 512. Data analysis is performed in the data processor 512. It is possible to include image data such as, for example, MRI (Magnetic Resonance Imaging), etc., in the data analysis. It is possible to include, for example, scalp potential information such as EEG (Electroencephalogram), etc., in the data analysis. For example, a data part 514 of the MRI, the EEG, etc., is connected with the data processor 512. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations described above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 19, the sensor part 301 is mounted to the head of a human body. The sensor part 301 may be mounted to the chest of the human body. Magnetocardiography is possible thereby. For example, the sensor part 301 may be mounted to the abdomen of a pregnant woman. The palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

According to the embodiment, the base body 302 may be flexible or may be substantially not flexible. In the example shown in FIG. 19, the base body 302 is a continuous membrane that is patterned into a hat-like configuration. The base body 302 may have a net configuration. For example, a good fit is obtained thereby. For example, the adhesion of the base body 302 to the human body is improved. The base body 302 may have a hard helmet-like configuration.

Figure 20:
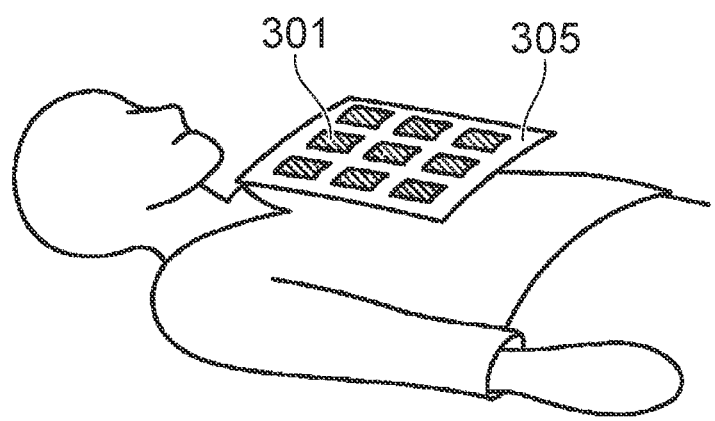
FIG. 20 is a schematic view showing the inspection device according to the third embodiment.

FIG. 20 is a schematic view showing the inspection device according to the third embodiment.

FIG. 20 is an example of a magnetocardiography device. In the example shown in FIG. 20, the sensor part 301 is provided on a hard base body 305 having a flat plate shape.

The input and output of the signal obtained from the sensor part 301 in the example shown in FIG. 20 is similar to the input and output described with reference to FIG. 19. The processing of the signal obtained from the sensor part 301 in the example shown in FIG. 20 is similar to the processing described with reference to FIG. 19.

There is a reference example in which a SQUID (Superconducting Quantum Interference Device) magnetic sensor is used as a device to measure a faint magnetic field such as a magnetic field emitted from a living body, etc. Because superconductivity is used in the reference example, the device is large; and the power consumption is large. The load on the measurement object (the patient) is large.

According to the embodiment, the device can be small. The power consumption can be suppressed. The load on the measurement object (the patient) can be reduced. According to the embodiment, the SN ratio of the magnetic field detection can be improved. The sensitivity can be increased.

Embodiments may include the following configurations (e.g., technological proposals).

Configuration 1

A magnetic sensor, comprising:

a first magnetic element;

a conductive member including a first corresponding portion, the first corresponding portion being along the first magnetic element;

an element current circuit configured to supply an element current to the first magnetic element; and a first current circuit configured to supply a first current to the first corresponding portion, the first current including an alternating current component, the first current including a first duration of a first current value of a first polarity, a first pulse duration of a first pulse current value of the first polarity, a second duration of a second current value of a second polarity, the second polarity being different from the first polarity, and a second pulse duration of a second pulse current value of the second polarity, an absolute value of the first pulse current value being greater than an absolute value of the first current value and greater than an absolute value of the second current value, an absolute value of the second pulse current value being greater than the absolute value of the first current value and greater than the absolute value of the second current value, the first pulse duration being less than the first duration and less than the second duration, the second pulse duration being less than the first duration and less than the second duration.

Configuration 2

The magnetic sensor according to Configuration 1, wherein the absolute value of the first pulse current value is not less than 10 times the absolute value of the first current value and not less than 10 times the absolute value of the second current value, and the absolute value of the second pulse current value is not less than 10 times the absolute value of the first current value and not less than 10 times the absolute value of the second current value.

Configuration 3

The magnetic sensor according to Configuration 1 or 2, wherein the first pulse duration is not less than 1 ns and not more than 1000 ns, and the second pulse duration is not less than 1 ns and not more than 1000 ns.

Configuration 4

The magnetic sensor according to any one of Configurations 1 to 3, wherein an electrical resistance of the first magnetic element increases as the absolute value of the first current value is increased, and the electrical resistance increases as the absolute value of the second current value is increased.

Configuration 5

A magnetic sensor, comprising:

a first magnetic element;

a conductive member including a first corresponding portion, the first corresponding portion being along the first magnetic element;

an element current circuit configured to supply an element current to the first magnetic element; and a first current circuit configured to supply a first current to the first corresponding portion, the first current including an alternating current component, the first current including a first duration of a first current value of a first polarity, and a second duration of a second current value of a second polarity, the second polarity being different from the first polarity, the element current including a first sub-duration of a first element value of the first polarity, a first sub-pulse duration of a first pulse element value of the first polarity, a second sub-duration of a second element value of the second polarity, and a second sub-pulse duration of a second pulse element value of the second polarity, the first sub-duration being a portion of the first duration, the first sub-pulse duration being an other portion of the first duration, the second sub-duration being a portion of the second duration, the second sub-pulse duration being an other portion of the second duration, an absolute value of the first pulse element value being greater than an absolute value of the first element value and greater than an absolute value of the second element value, an absolute value of the second pulse element value being greater than the absolute value of the first element value and greater than the absolute value of the second element value, the first sub-pulse duration being less than the first sub-duration and less than the second sub-duration, the second sub-pulse duration being less than the first sub-duration and less than the second sub-duration.

Configuration 6

The magnetic sensor according to Configuration 5, wherein the absolute value of the first pulse element value is not less than 10 times the absolute value of the first element value and not less than 10 times the absolute value of the second element value, and the absolute value of the second pulse element value is not less than 10 times the absolute value of the first element value and not less than 10 times the absolute value of the second element value.

Configuration 7

The magnetic sensor according to Configuration 5 or 6, wherein the first sub-pulse duration is not less than 1 ns and not more than 1000 ns, and the second sub-pulse duration is not less than 1 ns and not more than 1000 ns.

Configuration 8

The magnetic sensor according to any one of Configurations 5 to 7, wherein an electrical resistance of the first magnetic element increases as the absolute value of the first current value is increased, and the electrical resistance increases as the absolute value of the second current value is increased.

Configuration 9

The magnetic sensor according to any one of Configurations 1 to 8, wherein the first magnetic element includes:

a first magnetic layer;

a first counter magnetic layer; and a first nonmagnetic layer located between the first magnetic layer and the first counter magnetic layer.

Configuration 10

The magnetic sensor according to Configuration 9, wherein the first magnetic element includes a first layer including at least one selected from the group consisting of IrMn and PtMn, and the first magnetic layer is between the first layer and the first counter magnetic layer.

Configuration 11

The magnetic sensor according to Configuration 10, wherein the first magnetic element further includes an intermediate magnetic layer and an intermediate nonmagnetic layer, the intermediate magnetic layer is between the first layer and the first magnetic layer, and the intermediate nonmagnetic layer is between the intermediate magnetic layer and the first magnetic layer.

Configuration 12

The magnetic sensor according to Configuration 11, wherein the first nonmagnetic layer includes at least one selected from the group consisting of Cu, Au, and Ag, and the intermediate nonmagnetic layer includes Ru.

Configuration 13

The magnetic sensor according to any one of Configurations 1 to 12, wherein the first magnetic element includes a first end portion and a first other-end portion, the element current flows between the first end portion and the first other-end portion, a first length along a first direction of the first magnetic element is greater than a first width along a second direction of the first magnetic element, the first direction is along a direction from the first end portion toward the first other-end portion, and the second direction crosses the first direction.

Configuration 14

The magnetic sensor according to any one of Configurations 1 to 13, further comprising:

a second magnetic element;

a third magnetic element; and a fourth magnetic element, the first magnetic element including a first end portion and a first other-end portion, a direction from the first end portion toward the first other-end portion being along a first direction, the second magnetic element including a second end portion and a second other-end portion, a direction from the second end portion toward the second other-end portion being along the first direction, the third magnetic element including a third end portion and a third other-end portion, a direction from the third end portion toward the third other-end portion being along the first direction, the fourth magnetic element including a fourth end portion and a fourth other-end portion, a direction from the fourth end portion toward the fourth other-end portion being along the first direction,
the conductive member including
a second corresponding portion along the second magnetic element,
a third corresponding portion along the third magnetic element, and
a fourth corresponding portion along the fourth magnetic element,
the first corresponding portion including a first portion and a first other-portion,
the first portion corresponding to the first end portion,
the first other-portion corresponding to the first other-end portion,
the second corresponding portion including a second portion and a second other-portion,
the second portion corresponding to the second end portion,
the second other-portion corresponding to the second other-end portion,
the third corresponding portion including a third portion and a third other-portion,
the third portion corresponding to the third end portion,
the third other-portion corresponding to the third other-end portion,
the fourth corresponding portion including a fourth portion and a fourth other-portion,
the fourth portion corresponding to the fourth end portion,
the fourth other-portion corresponding to the fourth other-end portion,
the element current circuit being configured to supply the element current to the second, third, and fourth magnetic elements,
the first current circuit being configured to supply the first current to the second, third, and fourth corresponding portions.

Configuration 15
The magnetic sensor according to Configuration 14, wherein
the first other-end portion is electrically connected with the second end portion,
the first end portion is electrically connected with the third end portion,
the third other-end portion is electrically connected with the fourth end portion,
the second other-end portion is electrically connected with the fourth other-end portion,
the element current circuit is configured to supply the element current between a first connection point and a second connection point,
the first connection point is between the first end portion and the third end portion,
the second connection point is between the second other-end portion and the fourth other-end portion,
the first portion is electrically connected with the third portion,
the first other-portion is electrically connected with the second portion,
the third other-portion is electrically connected with the fourth portion,
the second other-portion is electrically connected with the fourth other-portion,
the first current circuit is configured to supply the first current between a fifth connection point and a sixth connection point,
the fifth connection point is between the first other-portion and the second portion, and
the sixth connection point is between the third other-portion and the fourth portion.

Configuration 16
The magnetic sensor according to Configuration 14 or 15, further comprising:
a detection circuit,
the detection circuit being configured to detect a change of a potential between a third connection point and a fourth connection point,
the third connection point being between the first other-end portion and the second end portion,
the fourth connection point being between the third other-end portion and the fourth end portion.

Configuration 17
The magnetic sensor according to any one of Configurations 1 to 13, further comprising:
a second magnetic element;
a first resistance element; and
a second resistance element,
the first magnetic element including a first end portion and a first other-end portion,
a direction from the first end portion toward the first other-end portion being along a first direction,
the second magnetic element including a second end portion and a second other-end portion,
a direction from the second end portion toward the second other-end portion being along the first direction,
the first resistance element including a third end portion and a third other-end portion,
a direction from the third end portion toward the third other-end portion being along the first direction,
the second resistance element including a fourth end portion and a fourth other-end portion,
a direction from the fourth end portion toward the fourth other-end portion being along the first direction,
the conductive member including
a second corresponding portion along the second magnetic element,
a third corresponding portion, and
a fourth corresponding portion,
the first corresponding portion including a first portion and a first other-portion,
the first portion corresponding to the first end portion,
the first other-portion corresponding to the first other-end portion,
the second corresponding portion including a second portion and a second other-portion,
the second portion corresponding to the second end portion,
the second other-portion corresponding to the second other-end portion,
the third corresponding portion including a third portion and a third other-portion,
the third portion corresponding to the third end portion,
the third other-portion corresponding to the third other-end portion,
the fourth corresponding portion including a fourth portion and a fourth other-portion,
the fourth portion corresponding to the fourth end portion,
the fourth other-portion corresponding to the fourth other-end portion,
the element current circuit being configured to supply the element current to the second magnetic element, the first resistance element, and the second resistance element,
the first current circuit being configured to supply the first current to the second, third, and fourth corresponding portions.

Configuration 18

The magnetic sensor according to Configuration 17, wherein the first end portion is electrically connected with the third end portion, the first other-end portion is electrically connected with the fourth end portion, the third other-end portion is electrically connected with the second end portion, the fourth other-end portion is electrically connected with the second other-end portion, the element current circuit is configured to supply the element current between a first connection point and a second connection point, the first connection point is between the first end portion and the third end portion, the second connection point is between the fourth other-end portion and the second other-end portion, the first portion is electrically connected with the second portion, the first other-portion is electrically connected with the second other-portion, the first current circuit is configured to supply the first current between a fifth connection point and a sixth connection point, the fifth connection point is between the first other-portion and the second other-portion, and the sixth connection point is between the first portion and the second portion.

Configuration 19

The magnetic sensor according to Configuration 17 or 18, further comprising:

a detection circuit, the detection circuit being configured to detect a change of a potential between a third connection point and a fourth connection point, the third connection point being between the first other-end portion and the fourth end portion, the fourth connection point being between the third other-end portion and the second end portion.

Configuration 20

An inspection device, comprising:

the magnetic sensor according to any one of Configurations 1 to 19; and a processor configured to process a signal output from the magnetic sensor.

According to embodiments, a magnetic sensor and an inspection device can be provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as magnetic elements, magnetic layers, non-magnetic layers, magnetic members, conductive members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and inspection devices practicable by an appropriate design modification by one skilled in the art based on the magnetic sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:

a first magnetic element;

a conductive member including a first corresponding portion, the first corresponding portion being along the first magnetic element;

an element current circuit configured to supply an element current to the first magnetic element; and a first current circuit configured to supply a first current to the first corresponding portion, the first current including an alternating current component, the first current including a first duration of a first current value of a first polarity, a first pulse duration of a first pulse current value of the first polarity, a second duration of a second current value of a second polarity, the second polarity being different from the first polarity, and a second pulse duration of a second pulse current value of the second polarity, an absolute value of the first pulse current value being greater than an absolute value of the first current value and greater than an absolute value of the second current value, an absolute value of the second pulse current value being greater than the absolute value of the first current value and greater than the absolute value of the second current value, the first pulse duration being less than the first duration and less than the second duration, the second pulse duration being less than the first duration and less than the second duration.

2. The sensor according to claim 1, wherein the absolute value of the first pulse current value is not less than 10 times the absolute value of the first current value and not less than 10 times the absolute value of the second current value, and the absolute value of the second pulse current value is not less than 10 times the absolute value of the first current value and not less than 10 times the absolute value of the second current value.

3. The sensor according to claim 1, wherein
the first pulse duration is not less than 1 ns and not more than 1000 ns, and
the second pulse duration is not less than 1 ns and not more than 1000 ns.

4. The sensor according to claim 1, wherein
an electrical resistance of the first magnetic element increases as the absolute value of the first current value is increased, and
the electrical resistance increases as the absolute value of the second current value is increased.

5. The sensor according to claim 1, wherein
the first magnetic element includes a first end portion and a first other-end portion,
the element current flows between the first end portion and the first other-end portion,
a first length along a first direction of the first magnetic element is greater than a first width along a second direction of the first magnetic element,
the first direction is along a direction from the first end portion toward the first other-end portion, and
the second direction crosses the first direction.

6. An inspection device, comprising:
the magnetic sensor according to claim 1; and
a processor configured to process a signal output from the magnetic sensor.

7. The sensor according to claim 1, wherein
the first magnetic element includes:
  a first magnetic layer;
  a first counter magnetic layer; and
  a first nonmagnetic layer located between the first magnetic layer and the first counter magnetic layer.

8. The sensor according to claim 7, wherein
the first magnetic element includes a first layer including at least one selected from the group consisting of IrMn and PtMn, and
the first magnetic layer is between the first layer and the first counter magnetic layer.

9. The sensor according to claim 8, wherein
the first magnetic element further includes an intermediate magnetic layer and an intermediate nonmagnetic layer,
the intermediate magnetic layer is between the first layer and the first magnetic layer, and
the intermediate nonmagnetic layer is between the intermediate magnetic layer and the first magnetic layer.

10. The sensor according to claim 9, wherein
the first nonmagnetic layer includes at least one selected from the group consisting of Cu, Au, and Ag, and
the intermediate nonmagnetic layer includes Ru.

11. The sensor according to claim 1, further comprising:
a second magnetic element;
a third magnetic element; and
a fourth magnetic element,
the first magnetic element including a first end portion and a first other-end portion,
a direction from the first end portion toward the first other-end portion being along a first direction,
the second magnetic element including a second end portion and a second other-end portion,
a direction from the second end portion toward the second other-end portion being along the first direction,
the third magnetic element including a third end portion and a third other-end portion,
a direction from the third end portion toward the third other-end portion being along the first direction,
the fourth magnetic element including a fourth end portion and a fourth other-end portion,
a direction from the fourth end portion toward the fourth other-end portion being along the first direction,
the conductive member including
  a second corresponding portion along the second magnetic element,
  a third corresponding portion along the third magnetic element, and
  a fourth corresponding portion along the fourth magnetic element,
the first corresponding portion including a first portion and a first other-portion,
the first portion corresponding to the first end portion,
the first other-portion corresponding to the first other-end portion,
the second corresponding portion including a second portion and a second other-portion,
the second portion corresponding to the second end portion,
the second other-portion corresponding to the second other-end portion,
the third corresponding portion including a third portion and a third other-portion,
the third portion corresponding to the third end portion,
the third other-portion corresponding to the third other-end portion,
the fourth corresponding portion including a fourth portion and a fourth other-portion,
the fourth portion corresponding to the fourth end portion,
the fourth other-portion corresponding to the fourth other-end portion,
the element current circuit being configured to supply the element current to the second, third, and fourth magnetic elements,
the first current circuit being configured to supply the first current to the second, third, and fourth corresponding portions.

12. The sensor according to claim 11, wherein
the first other-end portion is electrically connected with the second end portion,
the first end portion is electrically connected with the third end portion,
the third other-end portion is electrically connected with the fourth end portion,
the second other-end portion is electrically connected with the fourth other-end portion,
the element current circuit is configured to supply the element current between a first connection point and a second connection point,
the first connection point is between the first end portion and the third end portion,
the second connection point is between the second other-end portion and the fourth other-end portion,
the first portion is electrically connected with the third portion,
the first other-portion is electrically connected with the second portion,
the third other-portion is electrically connected with the fourth portion,
the second other-portion is electrically connected with the fourth other-portion,
the first current circuit is configured to supply the first current between a fifth connection point and a sixth connection point,
the fifth connection point is between the first other-portion and the second portion, and
the sixth connection point is between the third other-portion and the fourth portion.

13. The sensor according to claim 11, further comprising:
a detection circuit,
the detection circuit being configured to detect a change of a potential between a third connection point and a fourth connection point,
the third connection point being between the first other-end portion and the second end portion,
the fourth connection point being between the third other-end portion and the fourth end portion.

14. The sensor according to claim 1, further comprising:
a second magnetic element;
a first resistance element; and
a second resistance element,
the first magnetic element including a first end portion and a first other-end portion,
a direction from the first end portion toward the first other-end portion being along a first direction,
the second magnetic element including a second end portion and a second other-end portion,
a direction from the second end portion toward the second other-end portion being along the first direction,
the first resistance element including a third end portion and a third other-end portion,
a direction from the third end portion toward the third other-end portion being along the first direction,
the second resistance element including a fourth end portion and a fourth other-end portion,
a direction from the fourth end portion toward the fourth other-end portion being along the first direction,
the conductive member including
 a second corresponding portion along the second magnetic element,
 a third corresponding portion, and
 a fourth corresponding portion,
the first corresponding portion including a first portion and a first other-portion,
the first portion corresponding to the first end portion,
the first other-portion corresponding to the first other-end portion,
the second corresponding portion including a second portion and a second other-portion,
the second portion corresponding to the second end portion,
the second other-portion corresponding to the second other-end portion,
the third corresponding portion including a third portion and a third other-portion,
the third portion corresponding to the third end portion,
the third other-portion corresponding to the third other-end portion,
the fourth corresponding portion including a fourth portion and a fourth other-portion,
the fourth portion corresponding to the fourth end portion,
the fourth other-portion corresponding to the fourth other-end portion,
the element current circuit being configured to supply the element current to the second magnetic element, the first resistance element, and the second resistance element,
the first current circuit being configured to supply the first current to the second, third, and fourth corresponding portions.

15. The sensor according to claim 14, wherein
the first end portion is electrically connected with the third end portion,
the first other-end portion is electrically connected with the fourth end portion,
the third other-end portion is electrically connected with the second end portion,
the fourth other-end portion is electrically connected with the second other-end portion,
the element current circuit is configured to supply the element current between a first connection point and a second connection point,
the first connection point is between the first end portion and the third end portion,
the second connection point is between the fourth other-end portion and the second other-end portion,
the first portion is electrically connected with the second portion,
the first other-portion is electrically connected with the second other-portion,
the first current circuit is configured to supply the first current between a fifth connection point and a sixth connection point,
the fifth connection point is between the first other-portion and the second other-portion, and the sixth connection point is between the first portion and the second portion.

16. The sensor according to claim 14, further comprising:
a detection circuit,
the detection circuit being configured to detect a change of a potential between a third connection point and a fourth connection point,
the third connection point being between the first other-end portion and the fourth end portion,
the fourth connection point being between the third other-end portion and the second end portion.

17. A magnetic sensor, comprising:
a first magnetic element;
a conductive member including a first corresponding portion, the first corresponding portion being along the first magnetic element;
an element current circuit configured to supply an element current to the first magnetic element; and
a first current circuit configured to supply a first current to the first corresponding portion, the first current including an alternating current component,
the first current including
 a first duration of a first current value of a first polarity, and
 a second duration of a second current value of a second polarity, the second polarity being different from the first polarity,
the element current including
 a first sub-duration of a first element value of the first polarity,
 a first sub-pulse duration of a first pulse element value of the first polarity,
 a second sub-duration of a second element value of the second polarity, and
 a second sub-pulse duration of a second pulse element value of the second polarity,
the first sub-duration being a portion of the first duration,
the first sub-pulse duration being an other portion of the first duration,
the second sub-duration being a portion of the second duration,
the second sub-pulse duration being an other portion of the second duration,
an absolute value of the first pulse element value being greater than an absolute value of the first element value and greater than an absolute value of the second element value, an absolute value of the second pulse element value being greater than the absolute value of the first element value and greater than the absolute value of the second element value, the first sub-pulse duration being less than the first sub-duration and less than the second sub-duration, the second sub-pulse duration being less than the first sub-duration and less than the second sub-duration.

18. The sensor according to claim 17, wherein the absolute value of the first pulse element value is not less than 10 times the absolute value of the first element value and not less than 10 times the absolute value of the second element value, and the absolute value of the second pulse element value is not less than 10 times the absolute value of the first element value and not less than 10 times the absolute value of the second element value.

19. The sensor according to claim 17, wherein the first sub-pulse duration is not less than 1 ns and not more than 1000 ns, and the second sub-pulse duration is not less than 1 ns and not more than 1000 ns.

20. The sensor according to claim 17, wherein an electrical resistance of the first magnetic element increases as the absolute value of the first current value is increased, and the electrical resistance increases as the absolute value of the second current value is increased.

\* \* \* \* \*